US012746232B2

(12) United States Patent
Ogawa et al.

(10) Patent No.: US 12,746,232 B2
(45) Date of Patent: Sep. 29, 2026

(54) PATCH FOR ALLEVIATING OR TREATING SYMPTOMS OF NEURODEGENERATIVE DISEASE

(71) Applicant: NOBELPHARMA CO., LTD., Tokyo (JP)

(72) Inventors: Takayuki Ogawa, Fukuoka (JP); Kenta Nishimura, Saga (JP); Hiroaki Ueno, Saga (JP); Yuhei Tani, Saga (JP); Mieko Ogino, Kanagawa (JP); Koki Sato, Tokyo (JP); Hisanori Hatsukaiwa, Tokyo (JP); Katsunori Miyoshi, Tokyo (JP); Takahiro Inoue, Tokyo (JP)

(73) Assignee: NOBELPHARMA CO., LTD., Tokyo (JP)

( * ) Notice: Subject to any disclaimer, the term of this patent is extended or adjusted under 35 U.S.C. 154(b) by 478 days.

(21) Appl. No.: 18/023,036

(22) PCT Filed: Aug. 30, 2021

(86) PCT No.: PCT/JP2021/031712
§ 371 (c)(1),
(2) Date: Feb. 24, 2023

(87) PCT Pub. No.: WO2022/045335
PCT Pub. Date: Mar. 3, 2022

(65) Prior Publication Data

US 2023/0293510 A1 Sep. 21, 2023

(30) Foreign Application Priority Data

Aug. 31, 2020 (JP) ................................ 2020-145562

(51) Int. Cl.
*A61K 9/70* (2006.01)
*A61K 31/46* (2006.01)
*A61K 47/32* (2006.01)

(52) U.S. Cl.
CPC ............ *A61K 31/46* (2013.01); *A61K 9/7053* (2013.01); *A61K 47/32* (2013.01)

(58) Field of Classification Search
None
See application file for complete search history.

(56) References Cited

U.S. PATENT DOCUMENTS

2001/0006628 A1* 7/2001 Govil .................. A61K 9/7061 424/78.37
2002/0150613 A1 10/2002 Govil et al.
2006/0183796 A1 8/2006 Becher et al.
2007/0010550 A1* 1/2007 McKenzie ............. A61K 31/46 514/304
2008/0090808 A1* 4/2008 Volvovitz ........... A61K 31/4709 514/297
2009/0299304 A1 12/2009 Tang
2021/0145760 A1* 5/2021 Wiedersberg ........... A61P 25/00
2022/0160697 A1 5/2022 Ogawa et al.

FOREIGN PATENT DOCUMENTS

CN 1994307 A 7/2007
CN 110809466 A 2/2020
JP H11-060475 A 3/1999
JP 2006-516267 A 6/2006
JP 2015-083569 A 4/2015
JP 2020-525546 A 8/2020
WO 2019/002208 A1 1/2019
WO 2020/189323 A1 9/2020

OTHER PUBLICATIONS

Mato et al. "Management of drooling in disabled patients with scopolamine patches" 2010.*
"Atropine and Scopolamine For the Treatment of Sialorrhea", 2005.*
"Scolopamine Patch Withdrawal Syndrome" 2014.*
Scopolamine effects on memory retention in mice: A model of dementia? abstract, 1986.*
Modelling dementia: effects of scopolamine on memory and attention abstract, 1988.*
What happens when you take a drug?, 2009.*
Maeda M. et al., Jpn J Clin Pharmacol Ther, 2018, 49(2), pp. 53-58.
Gordon C, et al., J Clin Pharmacol., 1985, pp. 25: 407-412.
Talmi YP et al., Otolaryngol Head Neck Surg., 1990, vol. 103, No. 4, pp. 615-618.
Jongerius PH et al., Pediatrics, 2004, vol. 114, No. 3, pp. 620-627.
Brodtkorb E et al., J Mental Deficiency Res, 1988, pp. 32, 233-237.
Mato A et al., Br J Clin Pharmacol., 2010, 69, pp. 6, 684-688.
Gordon C et al., Aviation Space Environmental Medicine, 1986, pp. 236-240.
Montero, M.A. et al., "Control of drooling using transdermal scopolamine skin patches. A case report", Med Oral Patol Oral Cir Bucal., 2008, vol. 13, No. 1, pp. E27-E30, abstract, case report.
Morise, B.T. et al., "Scopolamine loaded in natural rubber latex as a future transdermal patch for sialorrhea treatment", International Journal of Polymeric Materials and Polymeric Biomaterials, 2019, vol. 68, No. 13, pp. 788-795, entire text.
ISR and Written Opinion issued in WIPO Patent Application No. PCT/JP2021/031712, Oct. 19, 2021, translation.

(Continued)

*Primary Examiner* — Susan T Tran

(74) *Attorney, Agent, or Firm* — GREENBLUM & BERNSTEIN, P.L.C.

(57) ABSTRACT

It is an object of the present invention to provide a novel patch for alleviating or treating the symptoms of neurodegenerative disease. According to the present invention, provided is a patch for alleviating or treating the symptoms of neurodegenerative disease, comprising a scopolamine salt and/or a hydrate thereof, wherein the application time of the patch per application is within 48 hours.

13 Claims, 8 Drawing Sheets

(56) References Cited

OTHER PUBLICATIONS

IPRP issued in International Patent Application No. PCT/JP2021/031712, dated Feb. 28, 2023, translation.
Extended European Search Report issued in European Patent Application No. 21861756.1, Aug. 12, 2024.
Ronning OM et al., "Transdermal Scopolamine to Reduce Salivation and Possibly Aspiration after Stroke", Journal of Stroke and Cerebrovascular Diseases, vol. 17, No. 5, 2008, pp. 328-329.
Office Action issued in TW Patent Application No. 110132068, Dec. 30, 2024, translation.
Catherine, A history of Novartis, Internet literature, retrieved from: https://pharmaphorum.com/articles/a-history-of-novartis, 2013.
Office Action issued in JP Patent Application No. 2022-545757, dated Apr. 15, 2025, translation.
Office Action issued in TW Patent Application No. 110132068, dated Apr. 18, 2025, translation.
Office Action issued in CN Patent Application No. 202180052935.2, dated Apr. 29, 2025, translation.
Decision of Rejection issued in TW Patent Application No. 110132068, Jul. 29, 2025, translation.
Office Action issued in CN Patent Application No. 202180052935.2, dated Oct. 30, 2025, translation.
Office Action issued in EP Patent Application No. 21861756.1, dated Nov. 3, 2025.
Decision on Rejection issued in CN Patent Application No. 202180052935.2, Mar. 31, 2026, translation.
Office Action issued in CA Patent Application No. 3,193,154, Jul. 14, 2026.
Office Action issued in AU Patent Application No. 2021331298, dated Jun. 16, 2026.

* cited by examiner

[Fig. 1]
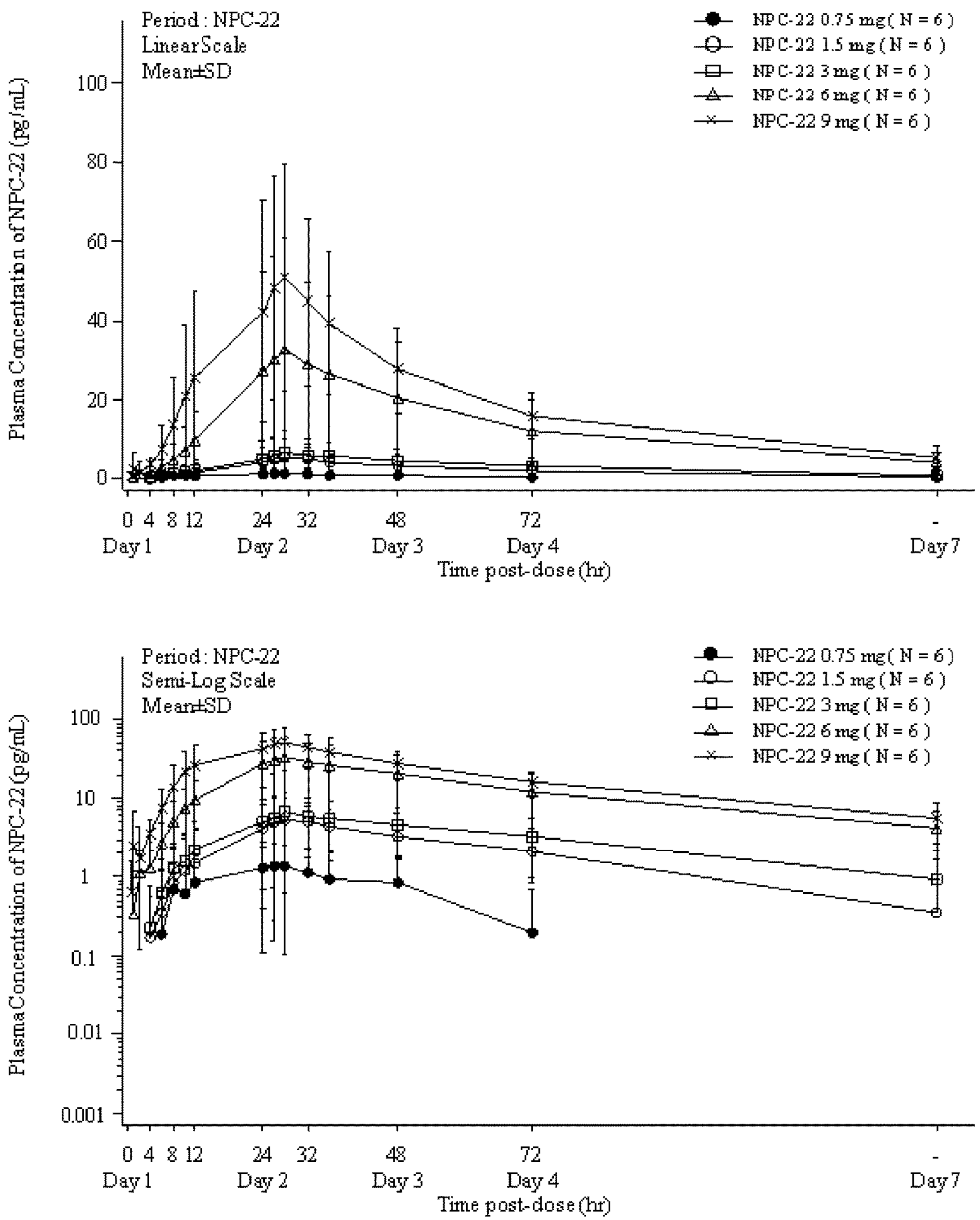

[Fig. 2]
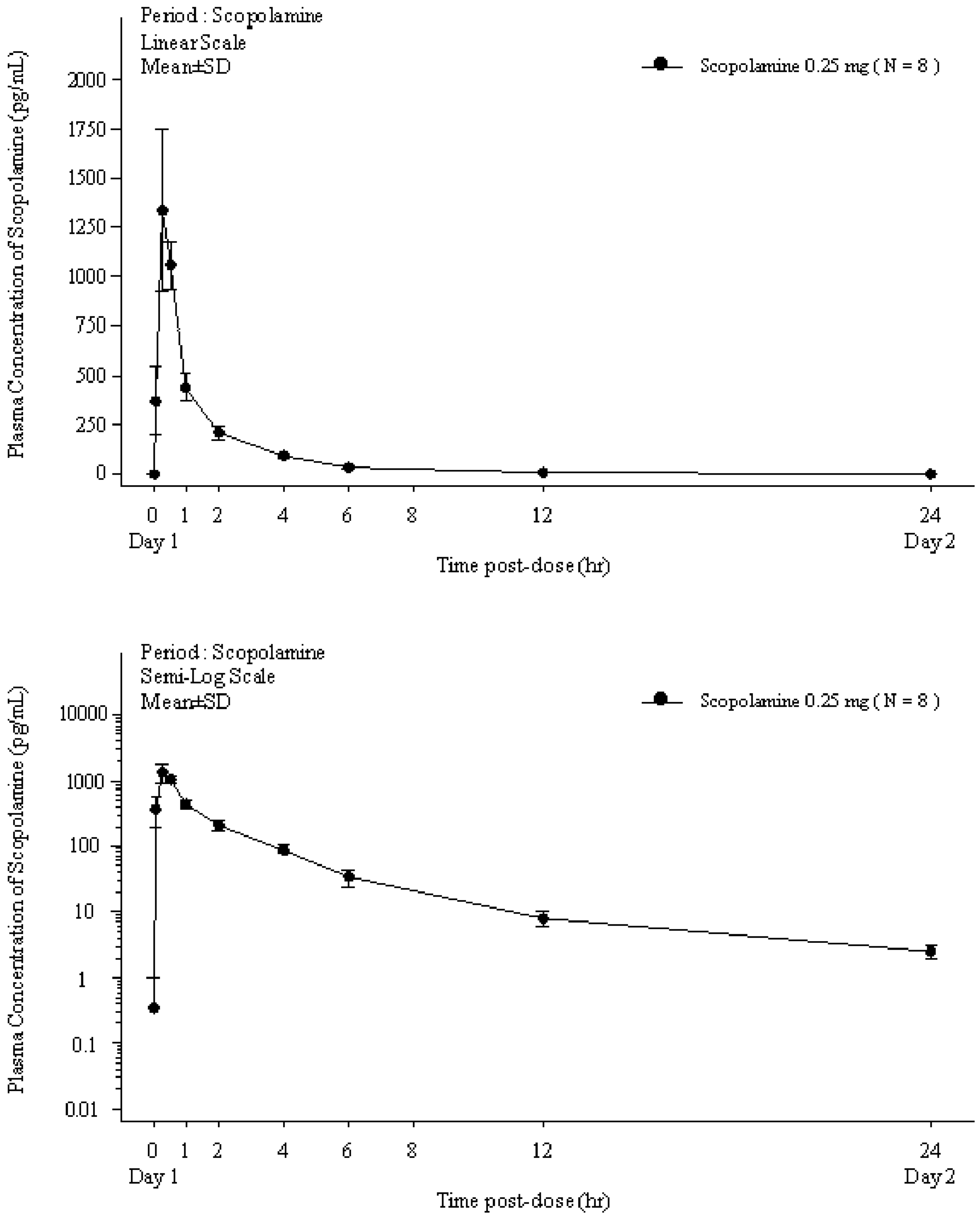

[Fig. 3]
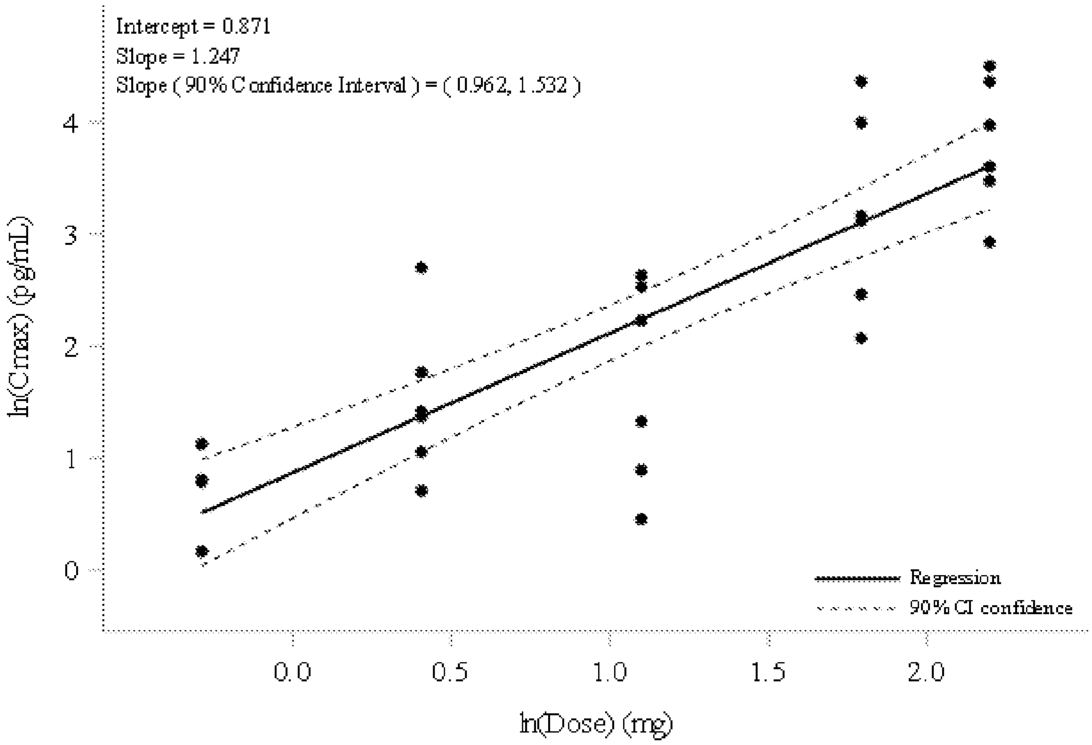
[Fig. 4]
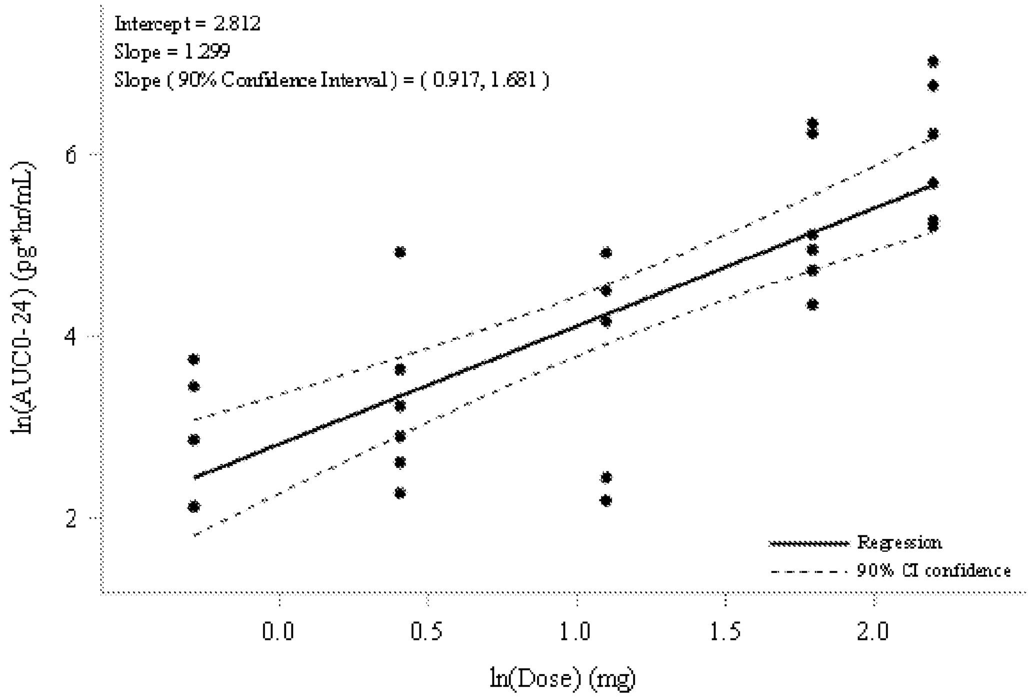

[Fig. 5]
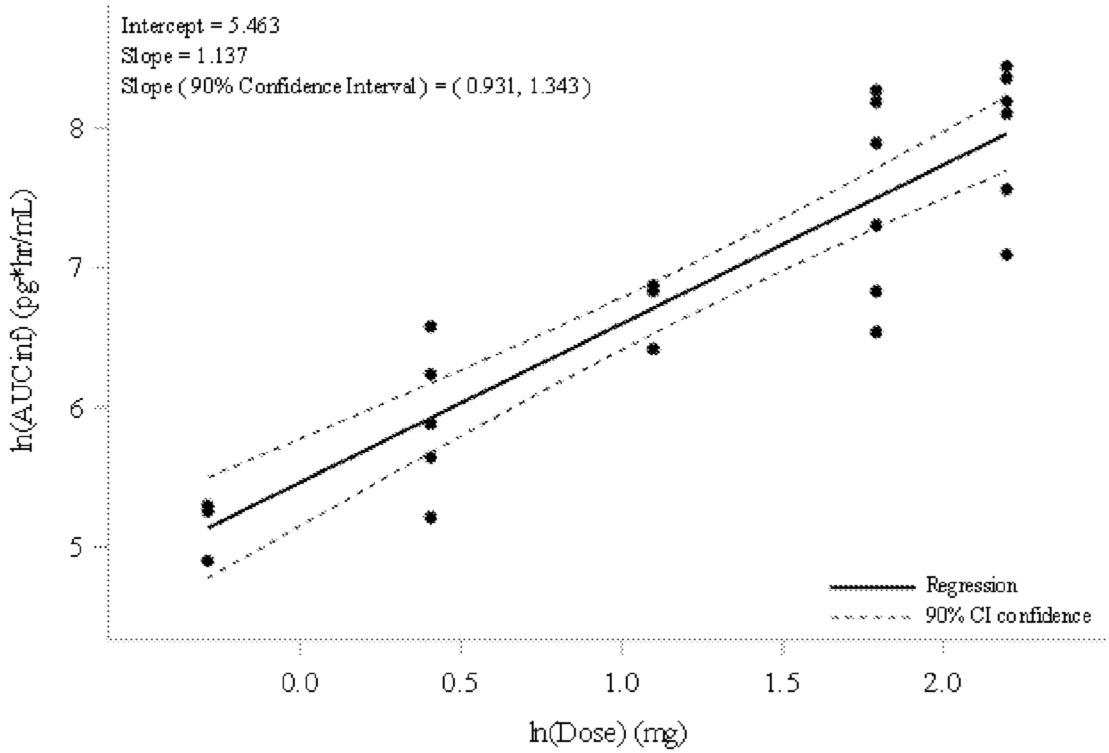
[Fig. 6]
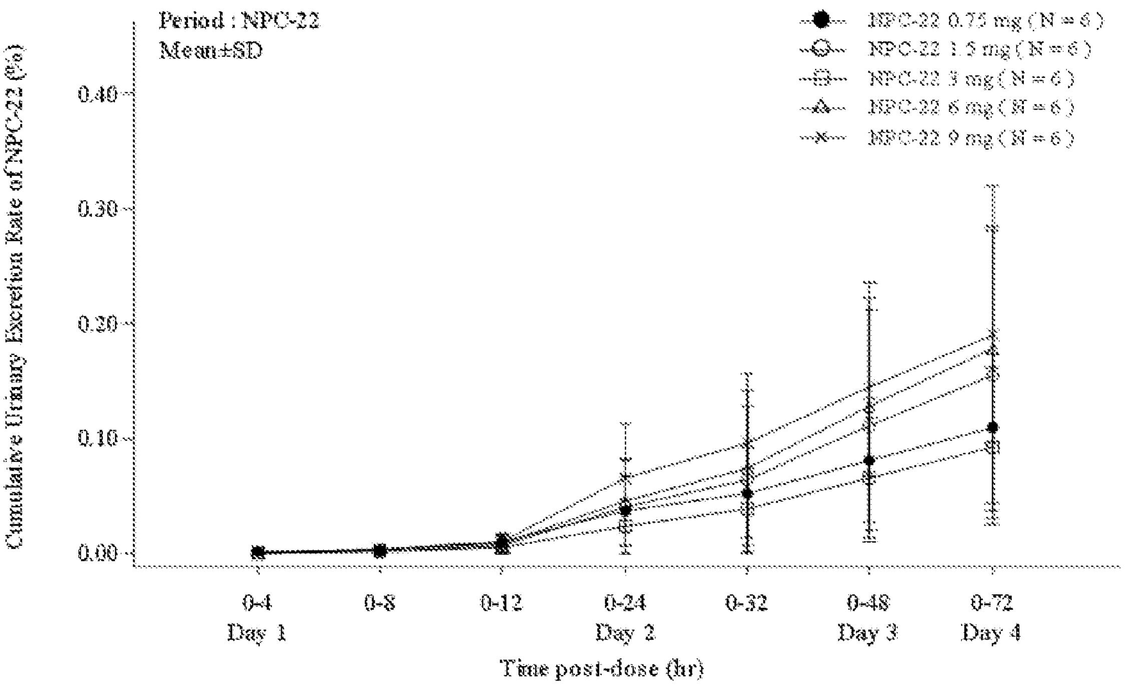

[Fig. 7]
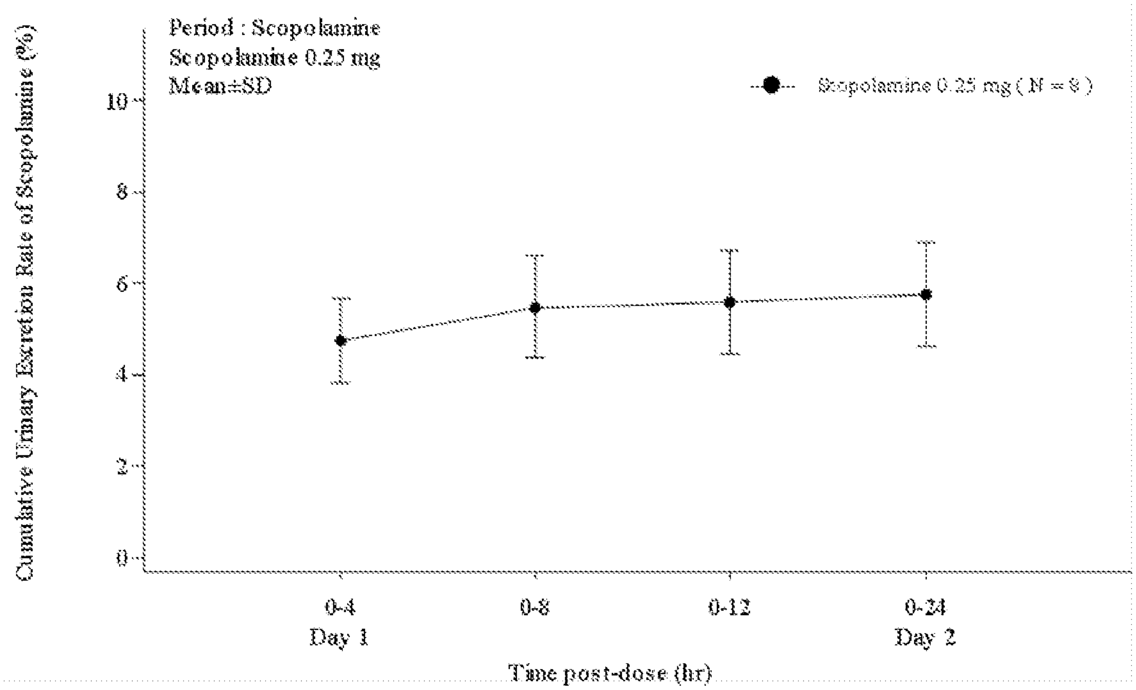

[Fig. 8]
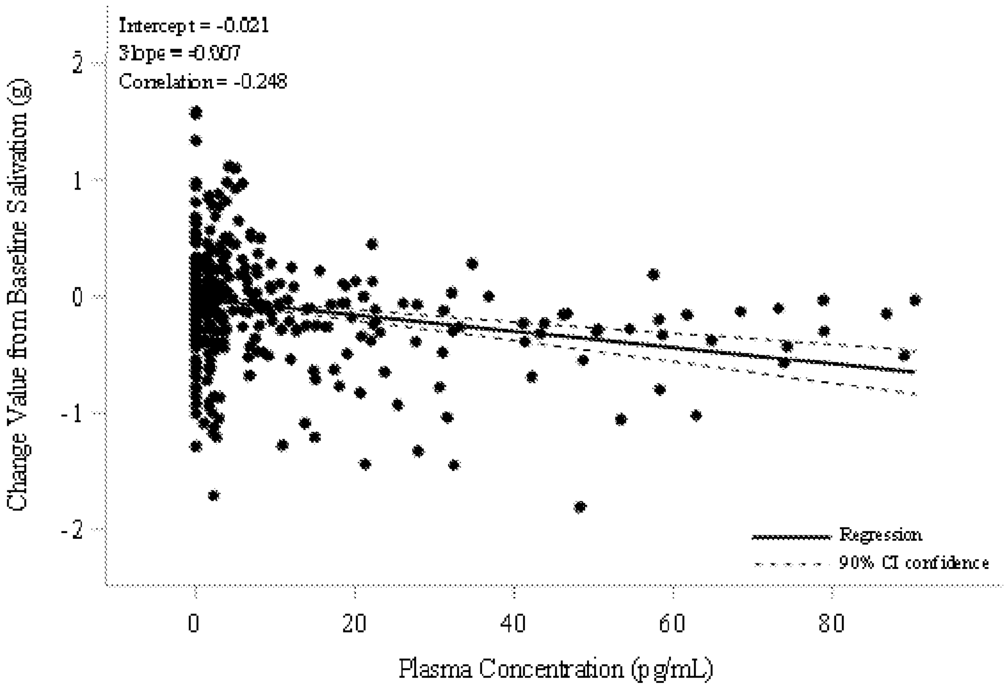
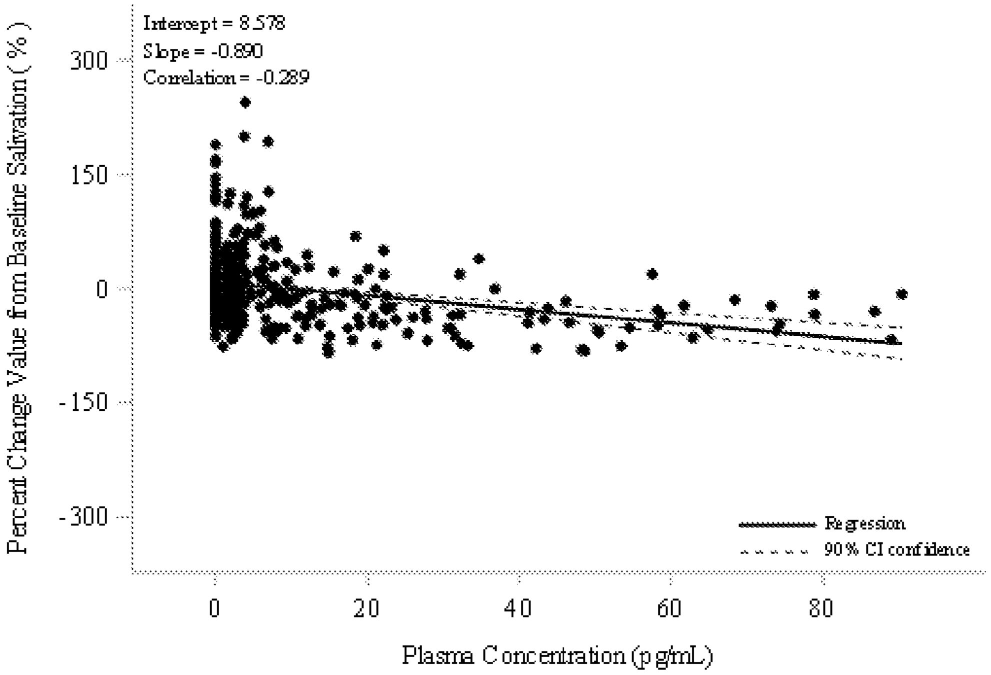

[Fig. 9]
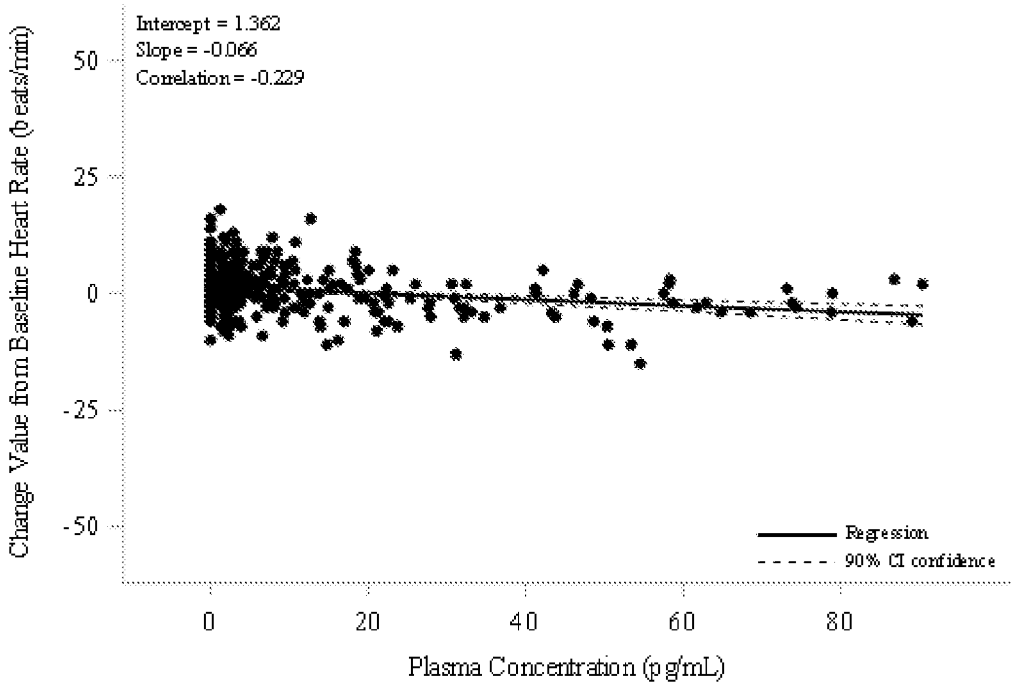
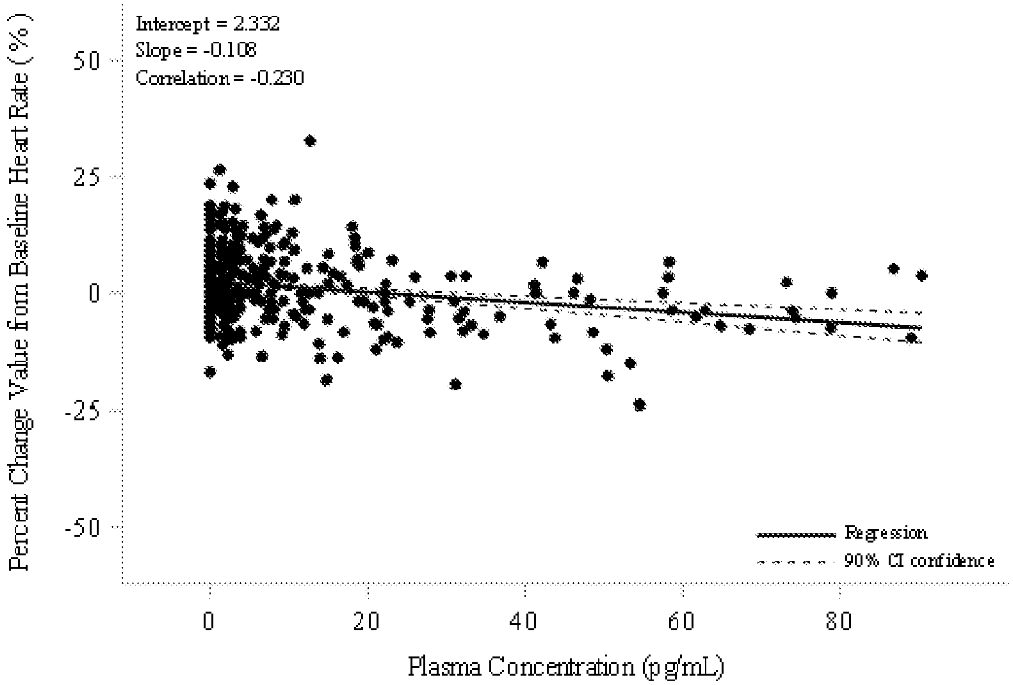

[Fig. 10]
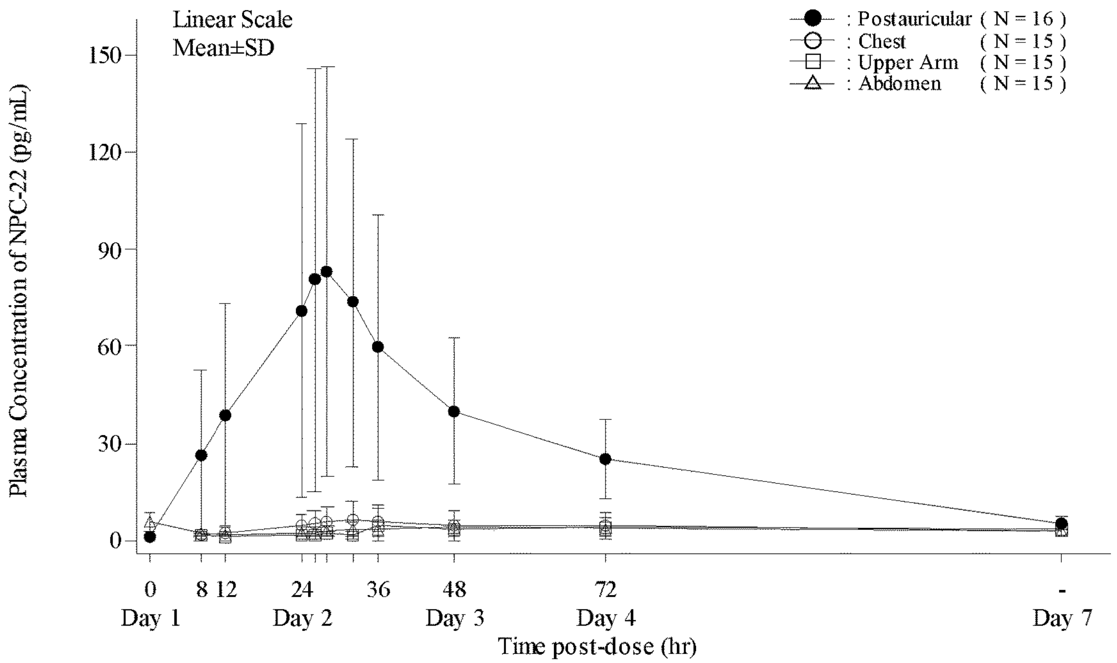

PATCH FOR ALLEVIATING OR TREATING SYMPTOMS OF NEURODEGENERATIVE DISEASE

TECHNICAL FIELD

The present invention relates to a patch for alleviating or treating the symptoms of neurodegenerative disease, wherein the patch comprises, as an active ingredient, a scopolamine salt and/or a hydrate thereof.

BACKGROUND ART

Scopolamine has been broadly known as an anticholinergic agent, and scopolamine is an agent having effects such as suppression of oral and/or tracheobronchial secretion and prevention of harmful parasympathetic nerve reflex. To date, pharmaceutical products containing scopolamine as an active ingredient have been developed. For example, in Japan, "Hysco (registered trademark) Subcutaneous Injection, KYORIN Pharmaceutical Co., Ltd." containing, as an active ingredient, scopolamine hydrobromide hydrate that is a scopolamine salt has been produced and marketed. In foreign countries, "Transderm Scop (registered trademark), Novartis" that is a patch containing, as an active ingredient, a scopolamine free base has been produced and marketed.

Non-Patent Document 1 suggests that a scopolamine ointment tends to decrease salivation. In addition, Non-Patent Documents 2 to 7 disclose that a scopolamine agent for transdermal administration decreases salivation.

PRIOR ART DOCUMENTS

Non-Patent Documents

Non-Patent Document 1: Maeda M et al., Jpn J Clin Pharmacol Ther 2018; 49(2): 53-58
Non-Patent Document 2: Gordon C et al., J Clin Pharmacol., 1985; 25: 407-412
Non-Patent Document 3: Talmi Y P et al., Otolaryngol Head Neck Surg., 1990, Vol. 103, No. 4, 615-618
Non-Patent Document 4: Jongerius P H et al., Pediatrics. 2004, Vol. 114, No. 3, 620-627
Non-Patent Document 5: Brodtkorb E et al., J Mental Deficiency Res., 1988, 32, 233-237
Non-Patent Document 6: Mato A et al., Br J Clin Pharmacol., 2010, 69: 6, 684-688
Non-Patent Document 7: Gordon C et al., Aviation Space Environmental Medicine. March 1986, 236-240

SUMMARY OF INVENTION

Problem to be Solved by the Invention

It is an object of the present invention to provide a novel patch for alleviating or treating the symptoms of neurodegenerative disease.

Means for Solving the Problem

The present inventors have conducted studies directed towards achieving the aforementioned problem. As a result, the present inventors have found that salivation can be reduced by transdermal application of a patch containing a scopolamine salt and/or a hydrate thereof, a polyvinyl pyrrolidone, and a base according to prescribed dosage and administration, and that this patch is useful for alleviating or treating the symptoms of neurodegenerative disease, thereby completing the present invention. According to the present invention, the following inventions are provided.

<1> A patch for alleviating or treating the symptoms of neurodegenerative disease, comprising a scopolamine salt and/or a hydrate thereof, wherein the application time of the patch per application is within 48 hours.

<2> The patch according to <1>, wherein the application time of the patch per application is within 24 hours.

<3> The patch according to <1>, wherein a single application that is within 48 hours is continuously repeated two or more times.

<4> The patch according to any one of <1> to <3>, wherein the applied dose of the scopolamine salt and/or the hydrate thereof per adult per day is 0.75 mg to 50 mg.

<5> The patch according to any one of <1> to <4>, which is applied to the postauricular, shoulder, upper arm, chest, abdomen, lower back, buttock, or thigh.

<6> The patch according to any one of <1> to <5>, wherein the scopolamine salt and/or the hydrate thereof are scopolamine hydrobromide and/or scopolamine hydrobromide hydrate.

<7> The patch according to any one of <1> to <6>, which further comprises a polyvinyl pyrrolidone and a base.

<8> The patch according to <7>, wherein the base is at least one type selected from amine compounds.

<9> The patch according to <8>, wherein the amine compound is a methyl methacrylate/butyl methacrylate/dimethylaminoethyl methacrylate copolymer.

<10> The patch according to any one of <1> to <8>, which comprises a support, a drug-containing adhesive layer, and a release liner, wherein the drug-containing adhesive layer comprises a pharmaceutical composition containing a scopolamine salt and/or a hydrate thereof, a polyvinyl pyrrolidone, and a base.

<11> The patch according to <10>, wherein the content of the scopolamine salt and/or the hydrate thereof is 0.5% to 10% by mass, with respect to the total mass of the pharmaceutical composition.

<12> The patch according to <10> or <11>, wherein the content of the polyvinyl pyrrolidone is 0.3% to 12% by mass, with respect to the total mass of the pharmaceutical composition.

<13> The patch according to any one of <10> to <12>, wherein the content of the base is 0.3% to 10% by mass, with respect to the total mass of the pharmaceutical composition.

<14> The patch according to any one of <10> to <13>, wherein the base component of the drug-containing adhesive layer is at least one type selected from an acrylic adhesive, a rubber adhesive, and a silicone adhesive.

<15> The patch according to any one of <10> to <14>, wherein the base component of the drug-containing adhesive layer is an acrylic adhesive.

<16> The patch according to <15>, wherein the acrylic adhesive is at least one type selected from a hydroxyl group-containing acrylic adhesive and a non-polar acrylic adhesive.

Advantageous Effects of Invention

The patch according to the present invention, comprising, as an active ingredient, a scopolamine salt and/or a hydrate thereof, can effectively suppress salivation, and is useful for alleviation or treatment of the symptoms of neurodegenerative disease such as amyotrophic lateral sclerosis (ALS).

BRIEF DESCRIPTION OF DRAWINGS

FIG. 1 shows a transition of the plasma concentration of scopolamine (upper view: normal scale; lower view: logarithmic scale), when NPC-22 was administered once (applied for 24 hours) to healthy male adult subjects.

FIG. 2 shows a transition of the plasma concentration of scopolamine (upper view: normal scale; lower view: logarithmic scale), when a scopolamine hydrobromide hydrate injection (0.25 mg) was subcutaneously administered once to healthy male adult subjects.

FIG. 3 shows studies of the dose proportionality of a pharmacokinetic parameter ($C_{max}$), when 0.75 mg, 1.5 mg, 3 mg, 6 mg or 9 mg of NPC-22 was administered once (applied for 24 hours).

FIG. 4 shows studies of the dose proportionality of a pharmacokinetic parameter ($AU_{0-24}$), when 0.75 mg, 1.5 mg, 3 mg, 6 mg or 9 mg of NPC-22 was administered once (applied for 24 hours).

FIG. 5 shows studies of the dose proportionality of a pharmacokinetic parameter ($AUC_{inf}$), when 0.75 mg, 1.5 mg, 3 mg, 6 mg or 9 mg of NPC-22 was administered once (applied for 24 hours).

FIG. 6 shows the cumulative urinary excretion rate of scopolamine (a mean value±standard deviation), when 0.75 mg, 1.5 mg, 3 mg, 6 mg or 9 mg of NPC-22 (scopolamine) was administered once (applied for 24 hours).

FIG. 7 shows the cumulative urinary excretion rate of scopolamine (a mean value±standard deviation), when a scopolamine hydrobromide hydrate injection (0.25 mg) was subcutaneously administered once.

FIG. 8 shows the relationship between the plasma scopolamine concentration and the change amount and change percentage of salivation.

FIG. 9 shows the relationship between the plasma scopolamine concentration and the change amount and change percentage of the heart rate (12-lead electrocardiogram).

FIG. 10 shows a transition of the plasma concentration of scopolamine (a mean value±standard deviation) in each administration site, when NPC-22 was administered once (applied for 24 hours) to healthy male adult subjects.

EMBODIMENTS OF CARRYING OUT THE INVENTION

The patch of the present invention is a patch for alleviating or treating the symptoms of neurodegenerative disease, comprising a scopolamine salt and/or a hydrate thereof, wherein the application time of the patch per application is within 48 hours.

Examples of the neurodegenerative disease may include amyotrophic lateral sclerosis (ALS), anxiety-related disorders (social anxiety disorder, anxiety disorder, obsessive-compulsive disorder, post-traumatic stress disorder (PTSD)), polyglutamine disease, retinitis pigmentosa, neurosis, convulsion, panic disorder, sleep disorder, depression, reactive depression, epilepsy, Parkinson's disease, Parkinson's syndrome, Down syndrome, schizophrenia, autonomic imbalance, Huntington's disease, Alzheimer's disease, Lewy body dementia, frontotemporal dementia, affective disorders (including depressive or bipolar disorders), migraine, tension-type headache, cluster headache, dissociative disorder, neuromyelitis optica, optic neuritis, acute disseminated (disseminated) encephalomyelitis, allergic encephalomyelitis, Marquifava-Binyami disease, Binswanger disease, progressive multifocal leukoencephalopathy, postinfectious encephalitis, central pontine myelination, adrenoleukodystrophy, multiple system atrophy, Krabbe disease, metachromatic leukodystrophy, Alexander disease, Canavan disease, Cockayne syndrome, Peliszeus-Merzbacher disease, Fuller's syndrome, Lowe's syndrome, spinal cord injury, transverse myelitis, spinocerebellar degeneration, chronic inflammatory demyelinating polyneuropathy, Guillain-Barre syndrome, phenylketonuria, Refsum disease, Charcot-Marie-Tooth disease, Gaucher disease, Niemann-Pick disease, multiple sclerosis, fragile X syndrome, autism, insomnia, nervous cough, psychogenic seizure, psychogenic syncope, chirospasm, spastic torticollis, and neuropathy.

The therapeutic effects of atrophic lateral sclerosis can be evaluated using Amyotrophic Lateral Sclerosis Functional Rating Scale-Revised (ALSFRS-R), etc.

A symptom of neurodegenerative disease may be an increase in the amount of saliva secreted. Alleviation or treatment of the symptoms of neurodegenerative disease may be a reduction in the amount of saliva secreted.

The application time of the patch of the present invention per application is within 48 hours, preferably within 36 hours, more preferably within 30 hours, and further preferably within 24 hours. The application time of the patch of the present invention per application is particularly preferably 24 hours.

A single application of the patch of the present invention that is within 48 hours (preferably within 36 hours, more preferably within 30 hours, and further preferably within 24 hours) can be continuously repeated two or more times. When such a single application is continuously repeated two or more times, the lower limit of the number of applications is not particularly limited, and it may be two or more times, 3 or more times, 4 or more times, 5 or more times, 6 or more times, or 7 or more times. The upper limit of the number of applications is not particularly limited, either, and it may be 100 or less times, 50 or less times, 40 or less times, 30 or less times, 20 or less times, or 10 or less times.

In the patch of the present invention, the applied dose of a scopolamine salt and/or a hydrate thereof per adult per day is preferably 0.75 mg to 50 mg, more preferably 0.75 mg to 30 mg, further preferably 0.75 mg to 20 mg, and particularly preferably 0.75 mg to 9 mg. A specific example of the dose of a scopolamine salt and/or a hydrate thereof per day is 0.75 mg, 1.5 mg, 3 mg, 6 mg, 9 mg, or 18 mg.

The site, to which the patch of the present invention is applied, is not particularly limited. Examples of such an application site may include postauricular, shoulder, upper arm, chest, abdomen, lower back, buttock, and thigh. The application site is preferably postauricular, upper arm, chest, or abdomen, and is particularly preferably postauricular.

The active ingredient used in the patch of the present invention is a salt of scopolamine ((-)-(S)-3-hydroxy-2-phenylpropionic acid (1R,2R,4S,7S,9S)-9-methyl-3-oxa-9-azatricyclo[3.3.1.0$^{2,4}$]non-7-ylester), and/or a hydrate thereof. Examples of the scopolamine salt may include acid-added salts with inorganic acids or organic acids, such as hydrochloride, hydrobromide, nitrate, phosphate, sulfate, acetate, ascorbate, benzoate, cinnamate, citrate, formate, fumarate, glutamate, lactate, maleate, malate, malonate, mandelate, methanesulfonate (mesylate), phthalate, salicylate, stearate, succinate, tartrate, propionate, butyrate, pamoate, and p-toluenesulfonate (tosylate), but the examples are not limited thereto. In the patch of the present invention, scopolamine hydrobromide and/or a hydrate thereof are preferably used.

The patch of the present invention may comprise a therapeutically effective amount of a scopolamine salt and/or a hydrate thereof, and the state thereof is not particularly limited. From the viewpoint of bioabsorbable properties, the state of a scopolamine salt and/or a hydrate thereof is preferably a dissolved state or an amorphous state. In order to administer a therapeutically effective amount of active ingredient to a patient, it is important to allow the patch of the present invention to comprise a predetermined amount of active ingredient.

The patch of the present invention is preferably a patch comprising a support, a drug-containing adhesive layer and a release liner, wherein the drug-containing adhesive layer comprises a pharmaceutical composition containing a scopolamine salt and/or a hydrate thereof, a polyvinyl pyrrolidone, and a base.

The content of a scopolamine salt and/or a hydrate thereof in the above-described pharmaceutical composition is 0.5% to 10% by mass, preferably 1% to 8% by mass, and more preferably 3% to 6% by mass, with respect to the total mass of the composition. If the content of the scopolamine salt and/or the hydrate thereof in the pharmaceutical composition is less than 0.5% by mass, it is likely that sufficient therapeutic effects cannot be obtained. On the other hand, if the content of the scopolamine salt and/or the hydrate thereof in the pharmaceutical composition exceeds 10% by mass, it is economically disadvantageous.

The above-described pharmaceutical composition contains a polyvinyl pyrrolidone in order to improve the chemical stability of scopolamine. A commonly used polyvinyl pyrrolidone has a weight average molecular weight of several thousands to several millions. One or more types of these polyvinyl pyrrolidones can be used.

The content of a polyvinyl pyrrolidone in the above-described pharmaceutical composition is in the range of 0.3% to 12% by mass, preferably 0.5% to 10% by mass, and more preferably 1% to 8% by mass, with respect to the total mass of the composition. If the content of the polyvinyl pyrrolidone in the above-described pharmaceutical composition is less than 0.3% by mass, it is likely that a sufficient chemical stability-improving effect cannot be obtained. On the other hand, if the content of the polyvinyl pyrrolidone in the above-described pharmaceutical composition exceeds 12% by mass, it is likely that the polyvinyl pyrrolidone unfavorably affects the physical properties of the composition. In addition, when the weight ratio of the polyvinyl pyrrolidone to the scopolamine salt and/or the hydrate thereof is 2 or greater, it is likely to affect the uniformity of the composition. Accordingly, the weight ratio of the polyvinyl pyrrolidone to the scopolamine salt and/or the hydrate thereof is preferably less than 2.

In order to convert the scopolamine salt and/or the hydrate thereof to a free base(s), and also in order to improve the chemical stability of scopolamine, the above-described pharmaceutical composition preferably contains an amine compound. The amine compound may be any of a primary amine, a secondary amine, and a tertiary amine. Examples of the primary amine may include, but are not limited to, methylamine, ethylamine, and dodecylamine. Examples of the secondary amine may include, but are not limited to, dimethylamine, diethylamine, and N-methylethanamine. Examples of the tertiary amine may include, but are not limited to, N,N-diethylmethylamine, tributylamine, N,N-dimethyl-p-toluidine, N,N-diethyl-p-toluidine, and a methyl methacrylate/butyl methacrylate/dimethylaminoethyl methacrylate copolymer. One or more types of these amine compounds can be used.

The content of an amine compound in the above-described pharmaceutical composition is in the range of 0.3% to 10% by mass, preferably 0.5% to 8.5% by mass, and more preferably 0.9% to 7.5% by mass, with respect to the total mass of the composition. If the content of the amine compound in the above-described pharmaceutical composition is less than 0.3% by mass, it is likely that sufficient bioabsorbable properties cannot be obtained. On the other hand, if the content of the amine compound in the above-described pharmaceutical composition exceeds 10% by mass, it is likely to affect chemical stability.

Examples of the patch of the present invention may include a matrix type patch and a reservoir type patch. The patch of the present invention may be either a matrix type patch or a reservoir type patch, but a matrix type patch is preferable because formulation design is easy and production costs can be reduced.

A matrix type patch consists of a support, a drug-containing adhesive layer, and a release liner.

The drug-containing adhesive layer contains a pharmaceutical composition comprising an active ingredient, and a base component. The base component used in this drug-containing adhesive layer is not particularly limited, and the base component is preferably an adhesive component generally used in patches, such as a rubber-based adhesive component, an acrylic adhesive component or a silicone-based adhesive component, and is particularly preferably an acrylic adhesive component; and a non-polar acrylic adhesive component and a hydroxyl group-containing acrylic adhesive component are further particularly preferable.

The acrylic adhesive component is a polymer or copolymer containing at least one type of (meth)acrylic acid ester.

The non-polar acrylic adhesive component does not have a functional group on the side chain in the monomer structural unit thereof. Examples of the non-polar acrylic adhesive component may include an alkyl (meth)acrylate polymer or copolymer, and an alkyl (meth)acrylate/vinyl acetate copolymer. Specific examples thereof may include, but are not limited to, a 2-ethylhexyl acrylate/2-ethylhexyl methacrylate/dodecyl methacrylate copolymer, a 2-ethylhexyl acrylate/vinyl acetate copolymer, and a methyl methacrylate/butyl methacrylate/dimethylaminoethyl methacrylate copolymer.

The hydroxyl group-containing acrylic adhesive component is a polymer or copolymer comprising, as a structural monomer, at least one type of (meth)acrylic acid ester containing a free hydroxyl group on the side chain in the monomer structural unit thereof. An example of the hydroxyl group-containing acrylic adhesive component may be a copolymer comprising (meth)acrylic acid hydroxyalkyl ester. Specific examples thereof may include, but are not limited to, a 2-ethylhexyl acrylate/hydroxylethyl acrylate/vinyl acetate copolymer, a 2-ethylhexyl acrylate/vinyl pyrrolidone/hydroxylethyl acrylate/vinyl acetate copolymer, a 2-ethylhexyl acrylate/hydroxylethyl acrylate/vinyl acetate copolymer, a 2-ethylhexyl acrylate/hydroxylethyl acrylate/glycidyl acrylate/vinyl acetate copolymer, a 2-ethylhexyl acrylate/vinyl acetate/2-hydroxyethyl acrylate copolymer, and a 2-ethylhexyl acrylate/vinyl acetate/2-hydroxyethyl acrylate/glycidyl methacrylate copolymer.

Taking into consideration the formation of a drug-containing adhesive layer and sufficient drug-releasing properties, the content of the base component in the drug-containing adhesive layer is 60% to 98.9% by mass, preferably 63% to 98% by mass, and more preferably 66% to 96% by mass, with respect to the total mass of the drug-containing adhesive layer. If the content of the base component in the drug-containing adhesive layer is less than 60% by mass, the physical properties of the patch, such as anchoring properties, are reduced. On the other hand, if the content of the base component exceeds 98.9%, the active ingredient and other additives cannot be sufficiently mixed into the patch, and thus, it is not favorable.

The drug-containing adhesive layer may also comprise an absorption promoter, as necessary. The absorption promoter may be any of compounds, which have been conventionally considered to have an action to promote absorption upon transdermal administration. Examples of the absorption promoter may include: fatty acids and the esters thereof, such as lauric acid, oleic acid, isostearic acid, isopropyl myristate, octyldodecyl myristate, glycerin oleic acid monoester, and hexyldecyl isostearate; alcohols and the esters or ethers thereof, such as oleyl alcohol, propylene glycol, and polyethylene glycol monooleate; sorbitan esters or ethers, such as sorbitan sesquioleate, polyoxyethylene sorbitan monooleate, sorbitan monolaurate, and sorbitan monooleate; phenol ethers such as polyoxyethylene nonylphenyl ether and polyoxyethylene octylphenyl ether; ionic surfactants such as castor oil or hardened castor oil, oleoyl sarcosine, lauric dimethyl aminoacetic acid betaine, and sodium lauryl sulfate; nonionic surfactants such as polyoxyethylene oleyl ether and polyoxyethylene lauryl ether; alkyl methyl sulfoxides such as dimethyl sulfoxide and decyl methyl sulfoxide; azacycloalkanes such as 1-dodecyl azacycloheptan-2-one and 1-geranyl azacycloheptan-2-one; and pyrrolidones excluding polyvinyl pyrrolidone.

The support used in the patch of the present invention is not particularly limited. For example, an elastic or non-elastic support that is impermeable to drugs can be used. Examples of the support may include: synthetic resin films or sheets, such as polyethylene, polypropylene, polybutadiene, an ethylene-vinyl acetate copolymer, polyvinyl chloride, polyester (polyethylene terephthalate, etc.), nylon and polyurethane, or laminates thereof; and porous bodies, foams, papers, woven fabrics, and non-woven fabrics.

The release liner used in the patch of the present invention is not particularly limited. For example, a release liner that is impermeable to drugs can be used. Examples of the release liner may include a film made of a polymer material such as polyethylene, polypropylene or polyester, a film on which aluminum is vapor-deposited, and a paper on which silicone oil or the like is applied. Among others, a polyester film is preferable because the active ingredient is not permeable through the polyester film, and also because the polyester film is advantageous in terms of workability and low costs; and a polyethylene terephthalate (PET) film is particularly preferable. Further, a laminate film formed by laminating a plurality of materials may also be used as such a release liner.

The patch of the present invention is preserved in a packaging material until use. The packaging material is not particularly limited, and examples thereof may include plastic films, metal (e.g., aluminum)-laminated plastic films, metal-deposited plastic films, ceramic (e.g., silicon oxide)-deposited plastic films, metal foils such as aluminum foils, metals such as stainless steel, and glasses. Among others, in terms of production costs and the like, it is preferable to use a metal-laminated plastic film, a metal-deposited plastic film, and the like.

In the patch of the present invention, further as needed, in order to control transdermal absorption of the active ingredient, a release-regulating membrane may be added to the skin application side of the drug-containing adhesive layer, or in order to apply the patch of the present invention to the skin, an adhesive layer may be added to the present patch.

The patch of the present invention preferably consists of a support, a drug-containing adhesive layer, and a release liner. The support has a thickness of 1 to 1000 μm, and preferably 10 to 700 μm; the drug-containing adhesive layer has a thickness of 10 to 200 μm, and preferably 30 to 150 μm; and the release liner has a thickness of 1 to 500 μm, and preferably 10 to 200 μm.

The patch of the present invention can be produced according to a known method for producing a patch. Examples of a preferred method for producing the patch of the present invention may include the following methods.

<Method 1>

A scopolamine salt and/or a hydrate thereof serving as an active ingredient, an amine compound, a polyvinyl pyrrolidone, a base component, and further as needed, an absorption promoter and the like are dissolved, for example, in an organic solvent such as ethyl acetate or methanol, or in a mixed solvent thereof. The thus dissolved matter is spread on a release liner or a support, and the organic solvent contained in the dissolved matter is evaporated to form a drug-containing adhesive layer. Thereafter, the drug-containing adhesive layer is adhered to the support or the release liner, thereby obtaining a patch.

<Method 2>

A scopolamine salt and/or a hydrate thereof serving as an active ingredient, an amine compound, a polyvinyl pyrrolidone, a base component, and further as needed, an absorption promoter and the like are melted by heating. The melted matter is spread on a release liner or a support, so as to form a drug-containing adhesive layer. Thereafter, the drug-containing adhesive layer is adhered to the support or the release liner, thereby obtaining a patch.

EXAMPLES

The present invention will be specifically described in the following examples.

However, these examples are not intended to limit the scope of the present invention.

Example 1

According to the mixing ratio shown in Table 1, scopolamine hydrobromide hydrate, isopropyl myristate, and dodecylamine were dissolved in a mixed solution of ethyl acetate and methanol, and thereafter, an acrylic adhesive component (product name: DURO-TAK 87-4287, manufactured by Henkel) was added to the mixed solution, followed by mixing and stirring, so as to obtain a homogeneously dissolved matter. Subsequently, using a doctor knife coater, this dissolved matter was spread on a release film, so that the thickness after drying became 100 μm. After that, the dissolved matter was dried to form a drug-containing adhesive layer, which was then adhered to a support. Thereafter, the obtained product was cut into a desired size, so as to obtain a patch.

Example 2

According to the mixing ratio shown in Table 1, a patch was obtained in the same manner as that of Example 1, with the exception that diethylamine was mixed instead of dodecylamine, such that the amount of the scopolamine free base became equal to that in Example 1.

Example 3

According to the mixing ratio shown in Table 1, a patch was obtained in the same manner as that of Example 1, with the exception that a methyl methacrylate/butyl methacrylate/dimethylaminoethyl methacrylate copolymer (product name: Eudragit EPO, manufactured by Evonik) was mixed instead of dodecylamine, such that the amount of the scopolamine free base became equal to that in Example 1.

Example 4

According to the mixing ratio shown in Table 1, a patch was obtained in the same manner as that of Example 1, with the exception that sodium hydroxide was mixed instead of dodecylamine, and polyvinyl pyrrolidone was further mixed, such that the amount of the scopolamine free base became equal to that in Example 1.

Example 5

According to the mixing ratio shown in Table 1, a patch was obtained in the same manner as that of Example 1, with the exception that Eudragit EPO was mixed instead of dodecylamine, and polyvinyl pyrrolidone was further mixed, such that the amount of the scopolamine free base became equal to that in Example 1.

Example 6

According to the mixing ratio shown in Table 1, scopolamine hydrobromide hydrate, Eudragit EPO, and polyvinyl pyrrolidone were dissolved in a mixed solution of ethyl acetate and methanol, and thereafter, DURO-TAK 87-4287 was added to the mixed solution, followed by mixing and stirring, so as to obtain a homogeneously dissolved matter.

Example 8

According to the mixing ratio shown in Table 1, scopolamine hydrobromide hydrate, isopropyl myristate, Eudragit EPO, and polyvinyl pyrrolidone were dissolved in a mixed solution of ethyl acetate and methanol, and thereafter, DURO-TAK 87-4287 was added to the mixed solution, followed by mixing and stirring, so as to obtain a homogeneously dissolved matter. Subsequently, using a doctor knife coater, this dissolved matter was spread on a release film, so that the thickness after drying became 100 μm. After that, the dissolved matter was dried to form a drug-containing adhesive layer, which was then adhered to a support. Thereafter, the obtained product was cut into a desired size, so as to obtain a patch.

Example 9

According to the mixing ratio shown in Table 1, scopolamine hydrobromide hydrate, isopropyl myristate, Eudragit EPO, and polyvinyl pyrrolidone were dissolved in a mixed solution of ethyl acetate and methanol, and thereafter, DURO-TAK 87-4287 was added to the mixed solution, followed by mixing and stirring, so as to obtain a homogeneously dissolved matter. Subsequently, using a doctor knife coater, this dissolved matter was spread on a release film, so that the thickness after drying became 50 μm. After that, the dissolved matter was dried to form a drug-containing adhesive layer, which was then adhered to a support. Thereafter, the obtained product was cut into a desired size, so as to obtain a patch.

Example 10

According to the mixing ratio shown in Table 1, a patch was obtained in the same manner as that of Example 9, with the exception that the mixed amount of isopropyl myristate was increased.

TABLE 1

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Scopolamine hydrobromide hydrate | 3 | 3 | 3 | 3 | 3 | 3 | 3 | 3 | 6 | 6 |
| DURO-TAK 87-4287 | 91 | 91.6 | 90.5 | 89.3 | 88 | 95 | 91 | 81 | 71 | 66 |
| Sodium hydroxide | — | — | — | 0.2 | — | — | — | — | — | — |
| Dodecylamine | 1 | — | — | — | — | — | — | — | — | — |
| Diethylamine | — | 0.4 | — | — | — | — | — | — | — | — |
| Eudragit EPO | — | — | 1.5 | — | 1.5 | 1 | 1 | 2 | 5 | 5 |
| Polyvinyl pyrrolidone | — | — | — | 2.5 | 2.5 | 1 | 5 | 4 | 8 | 8 |
| Isopropyl myristate | 5 | 5 | 5 | 5 | 5 | — | — | 10 | 10 | 15 |

Subsequently, using a doctor knife coater, this dissolved matter was spread on a release film, so that the thickness after drying became 100 μm. After that, the dissolved matter was dried to form a drug-containing adhesive layer, which was then adhered to a support. Thereafter, the obtained product was cut into a desired size, so as to obtain a patch.

Example 7

According to the mixing ratio shown in Table 1, a patch was obtained in the same manner as that of Example 6, with the exception that the mixed amount of polyvinyl pyrrolidone was increased.

<Test Example 1> Plasma Concentration Measurement Test Involving Single Transdermal Administration to Rats (Administration)

A scopolamine patch (Example 5) was administered to five male rats (Crl:CD (SD) strain: 6 weeks old at the time of administration) (Animal Nos. 10101 to 10105) via single transdermal administration (hermetically applied for 24 hours). Before administration on the administration date, the rats were depilated with an electric razor. After confirming the state of the dorsal portion, a test substance was applied onto the dorsal portion (i.e. the right side of the midline). The applied site was covered with a lint cloth (about 4.0 cm×4.0 cm), and was occluded by applying an elastic adhesive bandage thereto. The applied dose was set to be 1 patch/rat (content: 0.75 mg/1 patch). The area per patch was 2.5 $cm^2$/patch.

(Observation and Measurement)

Before administration on the administration date and at each time point of blood collection, the general condition was observed. Before administration on the administration date, the body weight was measured. At 4 time points, namely, at 3, 6, 12 and 24 hours after the administration, blood was collected, and the plasma scopolamine concentration was measured at 3, 6, 12 and 24 hours after the administration.

(Results)

The results obtained by measuring the plasma scopolamine concentration are shown in Table 2. The symbol * indicates that the measurement value exceeded the upper limit of quantification, and thus that the sample was analyzed again. Regarding a), Animal No. 10101 was excluded from the calculations of the mean value and SD. As shown in Table 2, scopolamine was detected in the plasma from 3 hours to 24 hours after the administration. $AUC_{0-24h}$ was 8659 pg·h/mL.

TABLE 2

| Animal | Scopolamine (pg/mL) | | | | $C_{max}$ | $T_{max}$ | $AUC_{0-24h}$ |
|---|---|---|---|---|---|---|---|
| No. | 3h | 6 h | 12 h | 24 h | (pg/ml) | (h) | (pg · h/ml) |
| 10101 | 3437* | 2169 * | 744.6* | 285.2 | 3437 | 3 | 28480 |
| 10102 | 329.5 | 414.3 | 313.4 | 186.1 | 414.3 | 6 | 6790 |
| 10103 | 71.23 | 147.5 | 167.2 | 139.7 | 167.2 | 12 | 3220 |
| 10104 | 36.10 | 59.15 | 84.71 | 100.1 | 100.1 | 24 | 1737 |
| 10105 | 49.93 | 105.1 | 158.9 | 169.0 | 169.0 | 24 | 3067 |
| Mean | 784.8 | 579.0 | 293.8 | 178.0 | 857.5 | 13.8 | 8659 |
| SD | 1487.6 | 899.5 | 265.3 | 69.2 | 1446.9 | 9.9 | 11238 |
| Mean[a)] | 121.7 | 181.5 | 181.1 | 148.7 | 212.7 | 16.5 | 3704 |
| SD[a)] | 139.3 | 159.3 | 95.7 | 37.7 | 138.2 | 9.0 | 2163 |

The observation results of the general conditions (observation time points: before administration on the administration date and at each time point of blood collection) and the body weight (g) before administration on the administration date are shown in Table 3 and Table 4, respectively. No abnormalities were found in the general conditions.

TABLE 3

| Animal | | (Frequency | Treatment | | | | |
|---|---|---|---|---|---|---|---|
| number | Findings | or time) | 1(Pre) | 1(3 h) | 1(6 h) | 1(12 h) | 2(24 h) |
| 10101 | | | — | — | — | — | — |
| 10102 | | | — | — | — | — | — |
| 10103 | | | — | — | — | — | — |
| 10104 | | | — | — | — | — | — |
| 10105 | | | — | — | — | — | — |

TABLE 4

| Animal number | Initial B.W. |
|---|---|
| 10101 | 183.7 |
| 10102 | 173.4 |
| 10103 | 184.1 |
| 10104 | 184.2 |
| 10105 | 177.8 |

Test Example 2

(Administration)

With respect to salivation induced by intravenous administration of pilocarpine hydrochloride to rats, the action of the patch of the present invention to suppress such salivation was examined. Ten male Crl:CD (SD) rats were used per group (6 weeks old at the time of administration). The following test groups were used: a control group (not administered), a scopolamine placebo formulation (a patch that did not comprise scopolamine), and 0.4, 1.2 and 3.6 mg/kg scopolamine patch (Example 5) (0.75 mg/2.5 $cm^2$ scopolamine hydrobromide hydrate) groups. Configuration of the groups is shown in the following Table 5.

TABLE 5

| Test group | Substance administered | Dose (mg/kg) | Number of animals | Animal No. |
|---|---|---|---|---|
| Control | Non | — | 10 | 1 to 10 |
| Base agent control | Scopolamine placebo | 0 | 10 | 11 to 20 |
| Low dose | Scopolamine | 0.4 | 10 | 21 to 30 |
| Intermediate dose | | 1.2 | 10 | 31 to 40 |
| High dose | | 3.6 | 10 | 41 to 50 |

The hair on the dorsal portion of each animal was depilated with an electric clipper and an electric razor. The administration site was marked with a permanent felt pen. Scopolamine placebo or scopolamine was applied onto the center of the hair-removed site. Thereafter, a non-woven adhesive bandage (MESHPORE (registered trademark), NICHIBAN CO., LTD.) that was slightly larger than the applied formulation was applied, so that it was overlapped on the formulation. After that, the applied site was occluded by winding an adhesive cloth elastic bandage (ELASTPORE Scopolamine, NICHIBAN CO., LTD.) on the applied site. For the control group, the hair-removed site was covered with a non-woven adhesive bandage (MESHPORE (registered trademark), NICHIBAN CO., LTD.) having the same size as that used for the formulation, and was then occluded by winding an adhesive cloth elastic bandage (ELASTPORE (registered trademark), NICHIBAN CO., LTD.) on the site. Subsequently, a mixed solution of 0.4 mg/kg medetomidine hydrochloride (Domitor (registered trademark), Nippon Zenyaku Kogyo Co., Ltd.)+2 mg/kg Midazolam (Midazolam Injection 10 mg, Fuji Chemicals industrial Co., Ltd.)+5 mg/kg butorphanol tartrate (Vetorphale (registered trademark), Meiji Seika Pharma Co., Ltd.) was intraperitoneally administered. In order to prevent suffocation due to saliva, the skin was excised under anesthesia, the trachea was exposed, and a cannula was inserted therein. Four hours after the patch administration (allowable range: within +10 minutes), in which the plasma concentration of scopolamine was increased and was stabilized, 1 mg/kg (2 mL/kg) pilocarpine hydrochloride was intravenously administered, and a swab whose weight had previously been measured using an electronic analytical scale (wherein 0.082 to 0.085 g of a swab was used) was inserted into the oval cavity. Thirty minutes after administration of the pilocarpine hydrochloride, the swab wetted with saliva was removed, and the weight thereof was promptly measured using an electronic analytical scale. The weight of the swab before the insertion was subtracted from the measured weight, and the obtained value was set to be the amount of saliva secreted. Besides, depending on the degree of salivation, the swab was exchanged with a new swab in the middle course of the experiment.

(Results and Consideration)

The results are shown in the following Table 6.1) indicates salivation 30 minutes after administration of the pilocarpine hydrochloride. *: P<0.05, **: P<0.01, a significant difference from the control group (Dunnett's multiple comparison test).

No statistically significant difference was found between the control group and the scopolamine placebo group, in terms of salivation. Salivation was significantly reduced in the 0.4 and 3.6 mg/kg scopolamine groups, compared with the control group. Salivation was not significantly reduced in the 1.2 mg/kg scopolamine group, compared with the control group. However, since salivation tended to be reduced in the 1.2 mg/kg scopolamine group, it was determined that a statistically significant reduction in salivation did not occur in the 1.2 mg/kg scopolamine group because of a variation in the plasma concentration of the test substance. From the aforementioned results, it was demonstrated that scopolamine exhibits an action to suppress pilocarpine-induced salivation when it is administered at a dose of 0.4 mg/kg or more.

TABLE 6

| Group | Animal No. | Salivation (g) [1)] |
|---|---|---|
| Control | 1 | 1.072 |
| | 2 | 1.115 |
| | 3 | 1.000 |
| | 4 | 1.243 |
| | 5 | 1.205 |
| | 6 | 1.351 |
| | 7 | 1.095 |
| | 8 | 1.035 |
| | 9 | 1.909 |
| | 10 | 1.469 |
| | mean | 1.249 |
| | ±S.D. | ±0.274 |
| Scopolamine Placebo | 11 | 1.293 |
| | 12 | 1.189 |
| | 13 | 1.094 |
| | 14 | 1.146 |
| | 15 | 1.414 |
| | 16 | 1.417 |
| | 17 | 1.088 |
| | 18 | 1.303 |
| | 19 | 1.243 |
| | 20 | 1.682 |
| | mean | 1.287 |
| | ±S.D | ±0.182 |
| Scopolamine 0.4 mg/kg | 21 | 0.521 |
| | 22 | 0.658 |
| | 23 | 1.243 |
| | 24 | 1.255 |
| | 25 | 0.737 |
| | 26 | 0.963 |
| | 27 | 0.928 |
| | 28 | 1.021 |
| | 29 | 0.795 |
| | 30 | 0.405 |
| | mean | 0.853 * |
| | ±S.D. | ±0.284 |

TABLE 6-continued

| Group | Animal No. | Salivation (g) [1)] |
|---|---|---|
| Scopolamine 1.2 mg/kg | 31 | 0.821 |
| | 32 | 0.928 |
| | 33 | 1.395 |
| | 34 | 1.968 |
| | 35 | 0.970 |
| | 36 | 0.945 |
| | 37 | 1.107 |
| | 38 | 1.169 |
| | 39 | 0.364 |
| | 40 | 1.085 |
| | mean | 1.075 |
| | ±S.D. | ±0.412 |
| Scopolamine 3.6 mg/kg | 41 | 0.663 |
| | 42 | 0.781 |
| | 43 | 0.674 |
| | 44 | 0.437 |
| | 45 | 0.330 |
| | 46 | 0.888 |
| | 47 | 0.605 |
| | 48 | 0.181 |
| | 49 | 0.845 |
| | 50 | 0.326 |
| | mean | 0.573 ** |
| | ±S.D. | ±0.242 |

<Clinical Test 1>

(Test Drugs)

Scopolamine patch: a patch containing 0.75 mg of scopolamine hydrobromide hydrate per patch (2.5 $cm^2$) (Example 10) (hereinafter also referred to as "NPC-22")

Scopolamine placebo: a formulation that does not contain scopolamine (active ingredient) but is apparently undistinguishable from the actual drug Scopolamine injection: an injection containing 0.5 mg of scopolamine hydrobromide hydrate in a single 1-mL syringe (Hysco Subcutaneous Injection)

(Dosage and Administration)

Scopolamine Groups

Case of Scopolamine Administration:

0.75 mg group: A single scopolamine patch is applied to the postauricular once for 24 hours.

1.5 mg group: Two scopolamine patches are applied to the postauricular once for 24 hours.

3 mg group: Four scopolamine patches are applied to the postauricular once for 24 hours.

6 mg group: Eight scopolamine patches are applied to the postauricular once for 24 hours.

9 mg group: Twelve scopolamine patches are applied to the postauricular once for 24 hours.

Case of Scopolamine Placebo Administration:

The placebo patches are applied to the postauricular once for 24 hours, depending on the number of patches applied at a dose of scopolamine patch administration.

Scopolamine Injection Group:

The scopolamine injection (0.25 mg) is subcutaneously administered once. Besides, the same subjects as those for the 3 mg scopolamine group are used.

(Administration Period)

A single administration is applied. The scopolamine patch is applied for 24 hours. In the case of scopolamine injection, it is subcutaneously administered once.

(Evaluation Items)

Scopolamine Patch Groups:

Safety: Adverse events, skin findings (according to the criteria of a patch test study group), vital signs, 12-lead electrocardiogram (including QT/QTc evaluation), and clinical test values Pharmacodynamics: Amount of saliva, salivation scores (VAS according to subjects), and heart rate (Holter electrocardiographic monitoring)

Pharmacokinetics: Plasma concentration of unchanged scopolamine, urinary excretion rate, and pharmacokinetic parameters ($C_{max}$, $T_{max}$, AUC, half-life, etc.)

Others: Amount of drug remaining in scopolamine patch

Scopolamine Injection Group:

Safety: Adverse events, vital signs, 12-lead electrocardiogram, and clinical test values Pharmacokinetics: Plasma concentration of unchanged scopolamine, urinary excretion rate, and pharmacokinetic parameters ($C_{max}$, $T_{max}$, AUC, half-life, etc.)

(Measurement of Amount of Saliva)

One hour before the measurement, the subject is allowed to lie down and is left at rest, and ingestion of food and drink is prohibited. Ten minutes before the measurement, the subject is allowed to take a sitting position, and thereafter, in order to collect saliva, absorbent cottons are fixed at a total of 3 sites, namely, between the right and left molars and the cheeks, and under the tongue, so that the absorbent cottons are allowed to absorb saliva. Salivation is calculated by measuring the weight of the absorbent cotton that absorbed saliva.

Measurement times: The measurement is carried out before administration, and 2, 4, 8, 12, 24 (after the measurement, the drug is removed), 26, 28, 32, 36, 48, and 72 hours after the administration. In addition, as a baseline, one day before the administration, the measurement is carried out at the same time as the measurement time on Day 1 of the administration. Besides, in the scopolamine injection group, the amount of saliva is not measured.

(Measurement of Plasma Concentration)

Unchanged scopolamine is measured.

Blood Collection Times:

Scopolamine patch groups: Blood is collected immediately before administration, and 0.5, 1, 2, 4, 6, 8, 10, 12, 24 (after the blood collection, the drug is removed), 26, 28, 32, 36, 48, 72 hours, and 7 days after the administration.

Scopolamine injection group: Blood is collected immediately before injection, and 0.08 (5 minutes), 0.25 (15 minutes), 0.5 (30 minutes), 1, 2, 4, 6, 12, and 24 hours after the injection.

(Urinary Excretion)

Unchanged scopolamine is measured.

Urine Collection Times:

Scopolamine patch groups: Urine is collected before administration (urine collected as needed), and 0 to 4, 4 to 8, 8 to 12, 12 to 24 (after the urine collection, the drug is removed), 24 to 32, 32 to 48, and 48 to 72 hours after the administration.

Scopolamine injection group: Urine is collected before administration (urine collected as needed), and 0 to 4, 4 to 8, 8 to 12, and 12 to 24 hours after the administration.

<Results of Clinical Test 1>

(1) Pharmacokinetic Analysis (1-1) Plasma Pharmacokinetics of Scopolamine (1-1-1) Transition of Plasma Concentration A transition of the plasma concentration of scopolamine (a mean value±standard deviation) when NPC-22 was administered once (applied for 24 hours) to healthy male adult subjects is shown in FIG. 1.

A transition of the plasma concentration of scopolamine (a mean value±standard deviation) when a scopolamine hydrobromide hydrate injection (0.25 mg) was administered to healthy male adult subjects via single subcutaneous administration is shown in FIG. 2.

After completion of the administration of NPC-22, the plasma scopolamine concentration increased during the application period, and such an increase in the plasma scopolamine concentration continued for several hours even after the peeling of NPC-22. Thereafter, from approximately 28 hours after the administration (4 hours after the peeling), the plasma scopolamine concentration gradually decreased. The plasma scopolamine concentration remained at a high concentration, together with an increase in the applied dose. In 1.5 mg or higher NPC-22 administration groups, even on Day 7 (Day 6 after the peeling), the plasma scopolamine concentration was found. In 6 and 9 mg NPC-22 administration groups, the plasma scopolamine concentration on Day 7 was a lower limit of quantification (1.0 pg/mL) or higher in all of the subjects, and the plasma scopolamine concentrations were about 13% and about 11% of the highest concentration, respectively. In 0.75 mg NPC-22 administration group, the plasma scopolamine concentrations of 2 out of the 6 subjects were less than a lower limit of quantification at all of the measurement time points.

The coefficient of variation (CV %) of the plasma scopolamine concentration was 42.2% to 90.6% upon the peeling of NPC-22 (24 hours after the administration), and thus, a large variation was found among the subjects.

After completion of the single subcutaneous administration of the scopolamine hydrobromide hydrate injection (0.25 mg), the plasma scopolamine concentration quickly increased, and 15 minutes after the administration, it reached the highest concentration that was 1337.5 pg/mL. Thereafter, the plasma scopolamine concentration monophasically decreased, and 24 hours after the administration, the plasma scopolamine concentration became 1/500 or less of the highest concentration.

(1-1-2) Pharmacokinetic Parameters

Plasma scopolamine pharmacokinetic parameters (a mean value and a standard deviation), when NPC-22 was administered once (applied for 24 hours) to healthy male adult subjects, are shown in Table 7. Besides, 2 cases in the 0.75 mg NPC-22 administration group, which were less than a lower limit of quantification at all of the measurement time points, were excluded from the analysis.

$C_{max}$, $AUC_{0-24}$, and $AUC_{inf}$ of the plasma scopolamine concentration after the single administration of NPC-22 (applied for 24 hours) increased together with an increase in the applied dose. The plasma scopolamine concentration ($C_{24}$) after the peeling of NPC-22 was about 69.6% to 88.6% of $C_{max}$, and $AUC_{inf}$ was about 6 to 16 times higher than $AUC_{0-24}$. In addition, $t_{max}$ was 23.1 to 36.8 hours after the administration, and $t_{1/2}$ was 42.0 to 54.8 hours.

TABLE 7

Pharmacokinetic parameters of plasma scopolamine concentration, when NPC-22 was administered once (applied for 24 hours) to healthy male adult subjects

| Parameters | Item | NPC-22 0.75 mg (N = 4)† | NPC-22 1.5 mg (N = 6) | NPC-22 3 mg (N = 6) | NPC-22 6 mg (N = 6) | NPC-22 9 mg (N = 6) |
|---|---|---|---|---|---|---|
| $C_{max}$ | Mean | 2.1798 | 5.6253 | 7.2780 | 33.230 | 51.758 |
| (pg/mL) | SD | 0.780418 | 4.72813 | 5.38211 | 27.7256 | 27.9633 |
| $C_{24hr}$ | Mean | 1.9323 | 4.2032 | 5.0663 | 27.437 | 42.452 |
| (pg/ml) | SD | 0.814845 | 3.80831 | 4.36953 | 24.5524 | 28.3844 |
| $t_{max}$ | Mean | 23.075 | 29.750 | 36.750 | 28.417 | 28.417 |
| (hr) | SD | 10.5188 | 3.6697 | 9.2664 | 1.9664 | 1.9664 |
| $AUC_{0-24}$ | Mean | 24.844 | 40.420 | 53.405 | 263.661 | 528.745 |
| (pg * hr/mL) | SD | 14.9873 | 48.7695 | 53.1738 | 217.7518 | 389.4911 |
| $AUC_{inf}$ | Mean | 175.294†† | 410.987††† | 836.009†† | 2217.600 | 3162.613 |
| (pg * hr/mL) | SD | 35.7553 | 210.4370 | 195.0340 | 1380.7735 | 1344.1697 |
| $t_{1/2}$ | Mean | 42.023†† | 54.846††† | 52.223†† | 48.719 | 42.593 |
| (hr) | SD | 16.2224 | 12.9088 | 29.5837 | 18.7734 | 12.4613 |

†Two subjects who were less than a lower limit of quantification at all of the measurement time points are excluded.

††n = 3,

†††n = 5

(1-1-3) Dose Proportionality

The dose proportionality of the plasma scopolamine concentration, when 0.75 mg, 1.5 mg, 3 mg, 6 mg or 9 mg of NPC-22 was administered once (applied for 24 hours) to the subjects, was examined according to a regression analysis [power model: ln ($C_{max}$ or AUC)=ln (a)+β/ln (Dose)]. Besides, 2 cases in the 0.75 mg NPC-22 administration group, which were less than a lower limit of quantification at all of the measurement time points, were excluded from the analysis. The results are shown in FIG. 3 to FIG. 5.

The point estimation values (90% confidence intervals) of β of $C_{max}$, $AUC_{0-24}$ and $AUC_{inf}$ were 1.247 (0.962 to 1.532), 1.299 (0.917 to 1.681), and 1.137 (0.931 to 1.343), respectively. The drug concentration was found to have linearity in the dose range of NPC-22 that was from 0.75 to 9 mg.

(1-1-4) Urinary Concentration and Excretion Rate of Scopolamine

A transition of the cumulative urinary excretion rate of scopolamine (a mean value±standard deviation), when NPC-22 was administered once (applied for 24 hours), is shown in FIG. 6.

The urinary excretion rate of scopolamine after administration of NPC-22 was low, and it was 0.024% to 0.065% until 24 hours after the administration, and was 0.093% to 0.190% until 72 hours after the administration. A large difference was not found in terms of the urinary excretion rate, regardless of the applied dose. In addition, a transition of the urinary excretion rate of scopolamine after the peeling of NPC-22 corresponded well to a transition of the plasma scopolamine concentration.

A transition of the cumulative urinary excretion rate of scopolamine (a mean value±standard deviation), when a scopolamine hydrobromide hydrate injection (0.25 mg) was administered via single subcutaneous administration, is shown in FIG. 7.

The urinary excretion rate of scopolamine was 5.767% until 24 hours after the subcutaneous administration of the scopolamine hydrobromide hydrate injection (0.25 mg), and this value was higher than the urinary excretion rate of scopolamine until 72 hours after the administration of NPC-22 (0.093% to 0.190%).

(1-1-5) Comparison Between NPC-22 and Scopolamine Hydrobromide Hydrate Injection in Terms of Exposure Level Using pharmacokinetic parameters ($C_{max}$, $t_{max}$, $AUC_{0-24}$, $AUC_{inf}$, and $t_{1/2}$), a comparison was made in terms of exposure level among a scopolamine subcutaneous administration group (total 8 subjects) and 3 mg to 9 mg NPC-22 administration groups. The results are shown in Table 8.

In the scopolamine subcutaneous administration group, plasma scopolamine $C_{max}$, $t_{max}$, $AUC_{inf}$, and $t_{1/2}$ of plasma scopolamine were 1388.7 pg/mL, 0.396 hours, 1796.253 pg*hr/mL, and 4.584 hours, respectively. When compared with the 3 mg to 9 mg NPC-22 administration groups, the $t_{max}$ and $t_{1/2}$ of the scopolamine subcutaneous administration group were shorter.

When the $C_{max}$ of the scopolamine subcutaneous administration group was compared with that of the 3 mg NPC-22 administration group, it was about 191 times higher. Moreover, the $AUC_{inf}$ of the scopolamine subcutaneous administration group was about 2.15 times higher than that of the 3 mg NPC-22 administration group. When the $C_{max}$ of the scopolamine subcutaneous administration group was compared with those of the 6 mg and 9 mg NPC-22 administration groups, the $C_{max}$ of the scopolamine subcutaneous administration group was about 42 times and about 27 times higher than those of the 6 mg and 9 mg NPC-22 administration groups, respectively. On the other hand, the $AUC_{inf}$ of the scopolamine subcutaneous administration group was about 0.81 times and about 0.57 times higher than those of the 6 mg and 9 mg NPC-22 administration groups, respectively, and thus, the 6 mg and 9 mg NPC-22 administration groups exhibited $AUC_{inf}$ values similar to that of the 0.25 mg subcutaneous administration group.

TABLE 8

Table 8: Comparison between scopolamine subcutaneous administration group and NPC-22 administration groups in terms of exposure level

| | | scopolamine | NPC-22 | | |
|---|---|---|---|---|---|
| Parameters | Item | 0.25 mg | 3 mg | 6 mg | 9 mg |
| $C_{max}$ | n | 8 | 6 | 6 | 6 |
| (pg/mL) | Mean | 1388.7 | 7.278 | 33.230 | 51.758 |
| | SD | 367.940 | 5.38211 | 27.7256 | 27.9633 |
| | Ratio† | — | 190.81 | 41.78 | 26.83 |
| $t_{max}$ | n | 8 | 6 | 6 | 6 |
| (hr) | Mean | 0.396 | 36.75 | 28.417 | 28.417 |
| | SD | 0.1157 | 9.2664 | 1.9664 | 1.9664 |
| | Difference†† | — | 36.35 | 28.02 | 28.02 |
| $AUC_{0-24}$ | n | 8 | 6 | 6 | 6 |
| (pg * hr/mL) | Mean | 1779.478 | 53.405 | 263.661 | 528.743 |
| | SD | 200.7941 | 55.1738 | 217.7518 | 389.4911 |
| | Ratio† | — | 33.32 | 6.75 | 3.37 |
| $AUC_{inf}$ | n | 8 | 3 | 6 | 6 |
| (pg * hr/mL) | Mean | 1796.253 | 836.009 | 2217.600 | 3162.613 |
| | SD | 199.5684 | 195.034 | 1380.7735 | 1344.1697 |
| | Ratio† | — | 2.15 | 0.81 | 0.57 |
| $t_{1/2}$ | n | 8 | 3 | 6 | 6 |
| (hr) | Mean | 4.584 | 52.223 | 48.719 | 42.593 |
| | SD | 1.1301 | 29.5837 | 18.7734 | 12.4613 |

†Ratio = (Scopolamine)/(NPC-22)
††Difference = (NPC-22) − (Scopolamine)

(2) Drug Dose, Drug Concentration, and Relationship Between Those and Reaction (2-1) Relationship Between Plasma Scopolamine Concentration and Salivation The measurement values of plasma scopolamine concentrations in all subjects of the NPC-22 administration groups, to which the NPC-22 tape was administered, and change amounts and change percentages from baseline salivations at the same time points as the measurement of the plasma scopolamine concentrations, are shown in scatter plots. The results obtained by calculating the values of a regression parameter, a correlation coefficient, and 90% confidence interval are shown in FIG. 8.

A weak negative correlation was found between the plasma scopolamine concentration and the change amount and change percentage of the salivation (correlation coefficients: −0.248 and −0.289). As the plasma scopolamine concentration increased, the salivation tended to decrease.

(2-2) Relationship Between Plasma Scopolamine Concentration and Heart Rate (12-Lead Electrocardiogram)

The measurement values of plasma scopolamine concentrations in all subjects of the NPC-22 administration groups, to which the NPC-22 tape was administered, and change amounts and change percentages from and baseline heart rates (12-lead electrocardiogram), are shown in scatter plots. The results obtained by calculating the values of a regression parameter, a correlation coefficient, and 90% confidence interval are shown in FIG. 9.

A weak negative correlation was found between the plasma scopolamine concentration and the change amount and change percentage of the heart rate (correlation coefficients: −0.229 and −0.230). As the plasma scopolamine concentration increased, the heart rate tended to decrease.

(3) Analysis of Residual Drug Amount

Analysis of Drug Amount Remaining in Formulation Recovered after Administration of NPC-22

Summary statistics of the residual amount and residual percentage of scopolamine hydrobromide hydrate in a formulation recovered after administration, when 0.75 mg, 1.5 mg, 3 mg, 6 mg or 9 mg of NPC-22 was administered once (applied for 24 hours), are shown in Table 9.

The mean residual percentage (the minimum and the maximum) of NPC-22 (0.75 mg/l patch) was 71.3% (58.3% and 79.8%), and the coefficient of variation (CV %) was 6.88%. Thus, a large variation was not found in the residual drug amount. Moreover, the mean absorption percentage (SD) of scopolamine estimated from the amount of the drug remaining in the formulation after the administration was 28.7% (4.90).

TABLE 9

Table 9: Summary of residual drug amount

| | | Residual | | Absorbed | |
|---|---|---|---|---|---|
| Treatment | Item | Amount (mg/sheet) | Percentage* (%) | Amount** (mg/sheet) | Percentage*** (%) |
| NPC-22 | N | 6 | 6 | 6 | 6 |
| 0.75 mg | Mean | 0.58028 | 74.56738 | 0.19792 | 25.43262 |
| | SD | 0.022038 | 2.831979 | 0.022038 | 2.831979 |
| | CV (%) | 3.80 | 3.80 | 11.14 | 11.14 |
| NPC-22 | N | 6 | 6 | 6 | 6 |
| 1.5 mg | Mean | 0.55837 | 71.75105 | 0.21983 | 28.24895 |
| | SD | 0.025391 | 3.262745 | 0.025391 | 3.262745 |
| | CV (%) | 4.55 | 4.55 | 11.55 | 11.55 |
| NPC-22 | N | 6 | 6 | 6 | 6 |
| 3 mg | Mean | 0.55715 | 71.59471 | 0.22105 | 28.40529 |
| | SD | 0.036407 | 4.678363 | 0.036407 | 4.678363 |
| | CV (%) | 6.53 | 6.53 | 16.47 | 16.47 |
| NPC-22 | N | 6 | 6 | 6 | 6 |
| 6 mg | Mean | 0.52630 | 67.63043 | 0.25190 | 32.36957 |
| | SD | 0.043458 | 5.584376 | 0.043458 | 5.584376 |
| | CV (%) | 8.26 | 8.26 | 17.25 | 17.25 |
| NPC-22 | N | 6 | 6 | 6 | 6 |
| 9 mg | Mean | 0.55333 | 71.10426 | 0.22487 | 28.89574 |
| | SD | 0.048224 | 6.196844 | 0.048224 | 6.196844 |
| | CV (%) | 8.72 | 8.72 | 21.45 | 21.45 |

<LOQ: Below the Lower Limit of Quantification, <LOQ is tabulated and calculated as 0
<LOQ: Below the Lower Limit of Quantification, <LOQ is tabulated and calculated as 0
*Residual Rate = (Residual Amount/Initial Amount) × 100 (%)
**Absorbed Amount = Initial Amount − Residual Amount
***Absorbed Rate = ((Initial Amount − Residual Amount)/Initial Amount) × 100 (%)

<Safety>

(1) Adverse Events and Side Effects

Adverse events and side effects expressed in the present test are shown in Table 10. Adverse events were found in 4/30 cases (13.3%) in the NPC-22 groups, 2/10 cases (20.0%) in the placebo group, and 5/8 cases (62.5%) in the scopolamine injection group. In all of these groups, neither severe adverse events, nor adverse events that resulted in suspension of the test, were found. If taking a look at individual NPC-22 dose groups, adverse events were found in 1/6 cases in the 0.75 mg NPC-22 administration group, 1/6 cases in the 1.5 mg NPC-22 administration group, 0/6 cases in the 3 mg NPC-22 administration group, 1/6 cases in the 6 mg NPC-22 administration group, and 1/6 cases in the 9 mg NPC-22 administration group. Among these, the case determined to be side effects was 1/6 cases in the 0.75 mg NPC-22 administration group. The side effects of the 0.75 mg NPC-22 administration group were an increase in the white blood cell count, a decrease in the lymphocyte count, and an increase in the neutrophil count, which were mild degrees of side effects found on Day 7 after the administration (on Day 6 after the peeling). These side effects each disappeared on Day 11 after the administration.

[Table 10]

TABLE 10

Adverse events and side effects

| Administration group | Name of adverse event | Causal relationship | Therapeutic treatment | Severity | Seriousness | Outcome |
|---|---|---|---|---|---|---|
| 0.75 mg | Increase in white blood cell count, increase in neutrophil count, decrease in lymphocyte count | Related | Non | Not severe | Mild | Recovered |
| 1.5 mg | Sore throat | Not related | Non | Not severe | Mild | Recovered |
| 6 mg | Itchiness and redness of chest site to which Holter electrocardiogram monitoring was applied | Not related | Non | Not severe | Mild | Recovered |
| 9 mg | KT 38.0° C., fatigue | Not related | Non | Not severe | Mild | Recovered |
| Placebo | Lightheadedness, nasal discharge, fatigue | Related | Non | Not severe | Mild | Recovered |
| | Nose bleeding | Not related | Non | Not severe | Mild | Recovered |
| | Reduction in blood pressure, bad mood, cold sweat | Related | Elevation of lower extremities | Not severe | Mild | Recovered |
| Scopolamine injection | Feeling dizzy | Related | Non | Not severe | Mild | Recovered |
| | Fatigue | Related | Non | Not severe | Mild | Recovered |
| | Heaviness of head | Related | Non | Not severe | Mild | Recovered |
| | Dry mouth | Related | Non | Not severe | Mild | Recovered |
| | Dry mouth | Related | Non | Not severe | Mild | Recovered |

(2) Skin Findings According to Criteria of Japanese Patch Test Study Group

Skin findings according to the criteria of a Japanese patch test study group are shown in Table 11.

In all judgment times, only "mild erythema" was observed. One hour after the peeling of the patch, mild erythema was observed in 6/6 subjects in the 0.75 mg NPC-22 administration group, 1/6 subjects in the 1.5 mg NPC-22 administration group, 2/6 subjects in the 3 mg NPC-22 administration group, 5/6 subjects in the 6 mg NPC-22 administration group, and 2/6 subjects in the 9 mg NPC-22 administration group. Twenty-four hours after the peeling of the patch, mild erythema was observed in 3/6, 0/6, 0/6, 0/6, and 2/6 subjects in the same above administration groups. Deterioration of the skin findings was not found with an increase in the applied dose, and thus, such mild erythema did not cause clinically significant problems. On the other hand, even in the skin findings in the placebo group, mild erythema was observed in 7/10 subjects one hour after the peeling of the patch, and in 2/10 subjects 24 hours after the peeling of the patch. Thus, the same levels of skin findings as those of the NPC-22 administration groups were obtained.

TABLE 11

| Skin findings | | | | | | | | | |
|---|---|---|---|---|---|---|---|---|---|
| Treatment | Day* | n | (−) | (+−) | (+) | (++) | (+++) | (++++) |
| NPC-22 | Day 2 | 6 | 0 | 6 | 0 | 0 | 0 | 0 |
| 0.75 mg | Day 3 | 6 | 3 | 3 | 0 | 0 | 0 | 0 |
| NPC-22 | Day 2 | 6 | 5 | 1 | 0 | 0 | 0 | 0 |
| 1.5 mg | Day 3 | 6 | 6 | 0 | 0 | 0 | 0 | 0 |
| NPC-22 | Day 2 | 6 | 4 | 2 | 0 | 0 | 0 | 0 |
| 3 mg | Day 3 | 6 | 6 | 0 | 0 | 0 | 0 | 0 |
| NPC-22 | Day 2 | 6 | 1 | 5 | 0 | 0 | 0 | 0 |
| 6 mg | Day 3 | 6 | 6 | 0 | 0 | 0 | 0 | 0 |
| NPC-22 | Day 2 | 6 | 4 | 2 | 0 | 0 | 0 | 0 |
| 9 mg | Day 3 | 6 | 4 | 2 | 0 | 0 | 0 | 0 |
| Placebo | Day 2 | 10 | 3 | 7 | 0 | 0 | 0 | 0 |
| | Day 3 | 10 | 8 | 2 | 0 | 0 | 0 | 0 |

*Day 2: 1 hour after peeling; Day 3: 24 hours after peeling

<Conclusion of Pharmacokinetics, Pharmacodynamics, Residual Drug Amount, and Results Regarding Safety>

After administration of NPC-22, the plasma scopolamine concentration was increased during the application period, and even after the peeling of NPC-22, such an increase in the plasma scopolamine concentration was continued for several hours. From approximately 28 hours after the administration (4 hours after the peeling) and afterwards, the plasma scopolamine concentration was gradually decreased. The plasma scopolamine concentration was shifted at high, together with an increase in the applied dose, and in the 1.5 mg or more administration groups, such a plasma scopolamine concentration was found even on Day 7 (on Day 6 after the peeling) in some cases.

The coefficient of variation (CV %) of the plasma scopolamine concentration at the time of peeling of NPC-22 (24 hours after the administration) was 42.2% to 90.6%, and thus, a large variation was found among the subjects.

The $C_{max}$, $AUC_{0-24}$, and $AUC_{inf}$ of the plasma scopolamine concentration after a single administration of NPC-22 were increased together with an increase in the applied dose. In the NPC-22 administration groups, $t_{max}$ was 23.1 to 36.8 hours after the administration, and $t_{1/2}$ was 42.0 to 54.8 hours. In addition, $AUC_{inf}$ was about 6 to 16 times higher than $AUC_{0-24}$. The dose proportionality obtained upon a single administration of NPC-22 was examined using a power model. As a result, the drug concentration was found to have linearity in the dose range of NPC-22 that was from 0.75 to 9 mg.

The urinary excretion rate of scopolamine was 0.093% to 0.190% until 72 hours after administration of NPC-22, and thus, only a little amount of scopolamine was excreted into the urine.

A transition of the urinary excretion rate after the peeling of NPC-22 corresponded well to a transition of the plasma scopolamine concentration.

The $C_{max}$ values of the scopolamine subcutaneous administration group were 191 times, 42 times, and 27 times higher than the $C_{max}$ values of the 3 mg, 6 mg, and 9 mg NPC-22 administration groups, respectively.

The $AUC_{inf}$ values of the scopolamine subcutaneous administration group were 2.15 times, 0.81 times, and 0.57 times higher than the $AUC_{inf}$ values of the 3 mg, 6 mg, and 9 mg NPC-22 administration groups, respectively.

A weak negative correlation was found between the plasma scopolamine concentration and the change amount and change percentage of salivation (correlation coefficients: −0.248 and −0.289). As the plasma scopolamine concentration increased, the salivation tended to decrease.

A weak negative correlation was found between the plasma scopolamine concentration and the change amount and change percentage of the heart rate (correlation coefficients: −0.229 and −0.230). As the plasma scopolamine concentration increased, the heart rate tended to decrease.

The mean residual percentage (the minimum and the maximum) of NPC-22 (0.75 mg/l patch) was 71.3% (58.3% and 79.8%), and the coefficient of variation (CV %) was 6.88%. Thus, a large variation was not found in the residual drug amount. Moreover, the mean absorption percentage (SD) of scopolamine estimated from the amount of the drug remaining in the formulation after the administration was 28.7% (4.90).

A dose-dependent increase in the adverse events of NPC-22 was not observed, and the degrees of the expressed adverse events were mild, and no problems were found regarding tolerability.

<Clinical Test 2>

(Test Drug)

Scopolamine patch: A patch containing 0.75 mg of scopolamine hydrobromide hydrate per patch (2.5 $cm^2$) (Example 10) (hereinafter also referred to as "NPC-22")

(Dosage and Administration)

9 mg of NPC-22 (i.e. 12 slices of NPC-22) is applied once to the postauricular, chest, upper arm, or abdomen of a single subject for 24 hours according to a crossover 4-site and 4-period study (open-label). The drug withdrawal period (a period from the peeling of the drug until the next drug application) is set to be 14 days.

(Administration Period)

A single administration is applied. The patch is applied for 24 hours.

(Evaluation Items)

Safety: Adverse events, skin findings (according to the criteria of a Japanese patch test study group), vital signs, 12-lead electrocardiogram, and clinical test Pharmacokinetics: Plasma concentration of unchanged scopolamine and pharmacokinetic parameters ($C_{max}$, $T_{max}$, AUC, half-life, etc.)

Others: Amount of drug remaining in scopolamine patch (Measurement of Plasma Concentration)

Unchanged scopolamine is measured.

Blood Collection Period:

Blood collection is carried out before administration, 8, 12, 24 (blood is collected before the peeling of the test drug), 26, 28, 32, 36, 48 and 72 hours after the administration, and on Day 7 and on Day 14 after the administration.

<Results of Clinical Test 2>

In the present test, one subject was suspended to participate in the test due to adverse events expressed upon drug administration to the postauricular during period 1 of the crossover study. Thus, administration to the chest, upper arm and abdomen, which was scheduled in period 2 and the subsequent periods, was suspended. Accordingly, the number of subjects for individual administration sites was 16 subjects (postauricular) and 15 subjects (chest, upper arm, or abdomen).

(1) Pharmacokinetic Analysis (1-1) Plasma Pharmacokinetics of Scopolamine (1-1-1) Transition of Plasma Concentration A transition of the plasma scopolamine concentration (a mean value±standard deviation) in each administration site, when NPC-22 was administered once (applied for 24 hours) to healthy male adult subjects, is shown in FIG. 10.

After completion of the administration of NPC-22 to the postauricular, the plasma scopolamine concentration increased during the application period, and such an increase in the plasma scopolamine concentration continued for several hours even after the peeling of NPC-22. Thereafter, from approximately 28 hours after the administration (4 hours after the peeling) and afterwards, the plasma scopolamine concentration gradually decreased.

In the case of administration of NPC-22 to chest, upper arm, and abdomen, other than the postauricular, the highest plasma concentration of scopolamine was an extremely low value in all of the sites, compares with the plasma scopolamine concentration in the postauricular. Disappearance from the plasma was also slow.

(1-1-2) Pharmacokinetic Parameters

Plasma scopolamine pharmacokinetic parameters (a mean value and a standard deviation) in individual administration sites, when NPC-22 was administered once (applied for 24 hours) to healthy male adult subjects, are shown in Table 12.

The $C_{max}$ and $AUC_{0-312}$ of the plasma scopolamine concentration were 85.093 pg/mL and 4716.497 pg·hr/mL, respectively, upon administration of NPC-22 to the postauricular. In the case of other administration sites, the $C_{max}$ and $AUC_{0-312}$ of the plasma scopolamine concentration were 3.5749 pg/mL to 6.8708 pg/mL and 522.618 pg·hr/mL to 756.356 pg·hr/mL, respectively. The $C_{max}$ and $AUC_{0-312}$ obtained upon administration of NPC-22 to the postauricular were extremely higher than those obtained upon administration of NPC-22 to the chest, upper arm, or abdomen. Moreover, $t_{1/2}$ was 38.774 hr in the case of the postauricular, whereas $t_{1/2}$ was 176.587 to 440.550 hr in the case of other administration sites. Thus, a large difference was found between the postauricular and other administration sites.

TABLE 12

Table 12: Pharmacokinetic parameters of plasma scopolamine concentration in each administration site, when NPC-22 was administered once (applied for 24 hours) to healthy male adult subjects

| | | Administration site | | | |
|---|---|---|---|---|---|
| Parameters | Item | Postauricular (N = 16) | Chest (N = 15) | Upper arm (N = 15) | Abdomen (N = 15) |
| $C_{max}$ | Mean | 85.093 | 6.8708 | 5.1898 | 3.1397 |
| (pg/ml) | SD | 65.7156 | 5.66702 | 4.97603 | 2.93913 |
| $C_{24\ hr}$ | Mean | 70.963 | 4.8119 | 0.45033 | 1.3514 |
| (pg/ml) | SD | 57.8117 | 3.40696 | 0.834412 | 1.62082 |
| $t_{max}$ | Mean | 29.125 | 53.996 | 98.933 | 52.800 |
| (hr) | SD | 5.3650 | 48.0268 | 80.6752 | 44.5985 |
| $AUC_{0-24}$ | Mean | 893.755 | 54.046 | 8.492 | 19.320 |
| (pg * hr/mL) | SD | 765.2272 | 36.2592 | 12.8236 | 24.2373 |
| $AUC_{0-312}$ | Mean | 4716.149 | 756.411 | 612.005 | 518.062 |
| (pg * hr/mL) | SD | 2707.3882 | 628.1665 | 497.6422 | 528.4440 |
| $AUC_{inf}$ | Mean | 4836.335[a] | 1038.360[b] | 1550.116[c] | 603.994[d] |
| (pg * hr/mL) | SD | 2473.9022[a] | 992.7000[b] | 65.8250[c] | 380.0449[d] |
| $t_{1/2}$ | Mean | 38.774[a] | 182.951[b] | 440.550[c] | 173.270[d] |
| (hr) | SD | 18.4110[a] | 364.3428[b] | 337.7319[c] | 131.1404[d] |

[a]n = 15,
[b]n = 11,
[c]n = 2, and
[d]n = 3

Calculation was carried out by setting BLQ (Below the Lower Limit of Quantification) to be '0'.

(2) Analysis of Residual Drug Amount

Drug Amount Remaining in Formulation Recovered after Administration of NPC-22

The residual drug percentage and the estimated absorption percentage were studied based on the formulation recovered after the administration of NPC-22.

The mean residual percentage of NPC-22 (0.75 mg/1 patch) in individual administration sites was 66.8 to 68.5%, and the coefficient of variation (CV %) was 6% to 9.29%.

Thus, a large variation was not found in the residual drug percentage. Moreover, the mean estimated absorption percentage of scopolamine estimated from the amount of the drug remaining in the formulation after the administration was 31.5% to 33.2%. No differences were found in terms of the mean residual percentage and the mean estimated absorption percentage, regardless of the administration sites.

<Safety>

(1) Adverse Events and Side Effects

Adverse events expressed in the present test are shown in Table 13.

Adverse events were found in 2/16 subjects (12.5%) upon administration to the postauricular, and 1/15 subjects (6.7%) upon administration to the abdomen. However, the adverse events occurring upon administration to the two administration sites were both mild, and neither severe adverse events, nor adverse events that resulted in suspension of the test, were found. In addition, the causal relationship of all of the adverse events with the drug was determined to be "not related." No adverse events were determined to be the side effects of the drug.

[Table 13]

TABLE 13

| Adverse events | | | | | | |
|---|---|---|---|---|---|---|
| Administration site | Name of adverse event | Causal relationship | Treatment | Severity | Seriousness | Outcome |
| Postauricular | Acute pharyngitis (due to transient infection) | Not related | Non | Not severe | Mild | Recovered |
| Postauricular | Arm muscle pain (due to push-up) | Not related | Non | Not severe | Mild | Recovered |
| Abdomen | CPK increase (due to long-term walking) | Not related | Non | Not severe | Mild | Recovered |
| Abdomen | AST increase (due to long-term walking) | Not related | Non | Not severe | Mild | Recovered |
| | LDH increase (due to long-term walking) | Not related | Non | Not severe | Mild | Recovered |

*1: A case that was suspended during drug administration to the postauricular, and thus, the drug was not administered to other sites.
*2: Test values on the day before administration: CPK: 124 U/L, AST: 23 U/L, LDH: 177 U/L (2) Skin Findings According to Criterial of Japanese Patch Test Study Group Criteria Skin findings according to the criteria of a Japanese patch test study group are shown in Table 14.

In all judgment times, the administration sites were all observed to have only "mild erythema (±)." One hour after the peeling of the patch, mild erythema was observed in 1/16 subjects upon administration to the postauricular, 4/15 subjects upon administration to the chest, 8/15 subjects upon administration to the upper arm, and 1/15 subjects upon administration to the abdomen. Twenty-four hours after the peeling of the patch, mild erythema was observed in 1/15 subjects upon administration to the upper arm. However, such mild erythema did not cause clinically significant problems.

TABLE 14

| Skin findings | | | | | | | | |
|---|---|---|---|---|---|---|---|---|
| Administration site | Day* | n | (−) | (+−) | (+) | (++) | (+++) | (++++) |
| postauricular | Day 2 | 16 | 15 | 1 | 0 | 0 | 0 | 0 |
| | Day 3 | 16 | 16 | 0 | 0 | 0 | 0 | 0 |
| chest | Day 2 | 15 | 11 | 4 | 0 | 0 | 0 | 0 |
| | Day 3 | 15 | 15 | 0 | 0 | 0 | 0 | 0 |
| upper arm | Day 2 | 15 | 7 | 8 | 0 | 0 | 0 | 0 |
| | Day 3 | 15 | 14 | 1 | 0 | 0 | 0 | 0 |
| abdomen | Day 2 | 15 | 14 | 1 | 0 | 0 | 0 | 0 |
| | Day 3 | 15 | 15 | 0 | 0 | 0 | 0 | 0 |

Adverse events occurred in one case upon administration to the postauricular, and the administration was suspended. Thus, regarding the one case, administration was not carried out to other sites.
*1: Day 2-1 hour after peeling; Day 3-24 hours after peeling
−: No reaction;
±: Mild erythema;
+: Erythema;
++: Erythema, edema and papules;
+++: Erythema, edema, papules and small blisters;
++++: Large blisters <Conclusion of Pharmacokinetics, Residual Drug Amount, and Results Regarding Safety>

When NPC-22 was administered once to individual administration sites, the plasma scopolamine concentration was shifted at high upon administration to the postauricular. On other hand, the plasma scopolamine concentration was shifted at extremely low upon administration to the chest, upper arm, and abdomen. The $C_{max}$ and AUC of the plasma scopolamine concentration upon administration to the postauricular were extremely high, compared with those upon administration to the chest, upper arm, and abdomen. The $C_{max}$ values upon administration to the postauricular were 12.4 times, 16.4 times and 27.1 times higher than the $C_{max}$ values upon administration to the chest, upper arm, and abdomen, respectively. The $AUC_{0-312}$ values upon administration to the postauricular were 6.2 times, 7.7 times and 9.1 times higher than the $AUC_{0-312}$ values upon administration to the chest, upper arm, and abdomen, respectively.

The mean residual percentage of NPC-22 that was recovered after it had been administered to the postauricular, chest, upper arm, and abdomen (applied for 24 hours) were 66.8% to 68.5%, and the mean estimated absorption percentage was 31.5% to 33.2%. A large difference was not found among the administration sites.

The adverse events expressed by administration of NPC-22 were all mild, and no problems were found regarding tolerability. Also, a large difference was not found among the administration sites. In addition, even regarding skin findings, only mild erythema was observed, which did not cause any clinically significant problems. A large difference was not found among the administration sites, either.

In a single NPC-22 administration test targeting healthy adults, which had been carried out prior to the present test, as the plasma scopolamine concentration increased, salivation tended to be reduced.

The adverse events and skin findings found in the present test were not largely different among the administration sites. However, the plasma scopolamine concentration obtained upon administration to the chest, upper arm or abdomen became extremely low, compared with the plasma scopolamine concentration obtained upon administration to the postauricular. Accordingly, it is adequate that the site to which NPC-22 is administered is determined to be the postauricular.

The invention claimed is:

1. A method for alleviating or treating excessive salivation due to neurodegenerative disease, which comprises applying to a postauricular of a patient in need thereof a patch comprising scopolamine hydrobromide hydrate, at a dosage of 1.5 to 9 mg per day, wherein the application time of the patch per application is within 48 hours,
- the patch comprises polyvinyl pyrrolidone and isopropyl myristate, and
- a weight ratio of the polyvinyl pyrrolidone to the scopolamine hydrobromide hydrate is less than 2.

2. The method according to claim 1, wherein the application time of the patch per application is within 24 hours.

3. The method according to claim 1, wherein a single application that is within 48 hours is continuously repeated two or more times.

4. The method according to claim 1, wherein the applied dose of the scopolamine salt and/or the hydrate thereof per adult per day is 6 to 9 mg.

5. The method according to claim 1, wherein the patch further comprises a base.

6. The method according to claim 5, wherein the base is at least one type selected from amine compounds.

7. The method according to claim 6 wherein the amine compound is a methyl methacrylate/butyl methacrylate/dimethylaminoethyl methacrylate copolymer.

8. The method according to claim 1, wherein the patch comprises a support, a drug-containing adhesive layer, and a release liner, wherein the drug-containing adhesive layer comprises a pharmaceutical composition containing a scopolamine salt and/or a hydrate thereof, a polyvinyl pyrrolidone, and a base.

9. The method according to claim 8, wherein the content of the scopolamine salt and/or the hydrate thereof is 0.5% to 10% by mass, with respect to the total mass of the pharmaceutical composition.

10. The method according to claim 8, wherein the content of the polyvinyl pyrrolidone is 0.3% to 12% by mass, with respect to the total mass of the pharmaceutical composition.

11. The method according to claim 8, wherein the content of the base is 0.3% to 10% by mass, with respect to the total mass of the pharmaceutical composition.

12. The method according to claim 8, wherein the base component of the drug-containing adhesive layer is at least one type selected from an acrylic adhesive, a rubber adhesive, and a silicone adhesive.

13. The method according to claim 8, wherein the base component of the drug-containing adhesive layer is an acrylic adhesive.

* * * * *